(12) United States Patent
Kroll et al.

(10) Patent No.: US 7,480,531 B1
(45) Date of Patent: Jan. 20, 2009

(54) SYSTEM AND METHOD FOR REDUCING PAIN ASSOCIATED WITH CARDIOVERSION SHOCKS GENERATED BY IMPLANTABLE CARDIAC STIMULATION DEVICES

(75) Inventors: Mark W. Kroll, Orono, MN (US); J. Christopher Moulder, Encino, CA (US)

(73) Assignee: Pacesetter, Inc., Sylmar, CA (US)

( * ) Notice: Subject to any disclaimer, the term of this patent is extended or adjusted under 35 U.S.C. 154(b) by 416 days.

(21) Appl. No.: 11/366,740

(22) Filed: Mar. 1, 2006

Related U.S. Application Data

(63) Continuation-in-part of application No. 11/005,976, filed on Dec. 6, 2004, which is a continuation-in-part of application No. 10/855,654, filed on May 26, 2004, now Pat. No. 7,155,286.

(51) Int. Cl.
*A61N 1/39* (2006.01)
(52) U.S. Cl. ............................ 607/5; 607/63; 607/72; 607/74
(58) Field of Classification Search .................. 607/5, 607/72, 74, 63
See application file for complete search history.

(56) References Cited

U.S. PATENT DOCUMENTS

| | | | |
|---|---|---|---|
| 4,869,252 A | 9/1989 | Gilli | 128/419 PG |
| 5,441,521 A | 8/1995 | Hedberg | |
| 5,634,938 A | 6/1997 | Swanson et al. | |
| 5,725,560 A | 3/1998 | Brink | |
| 5,782,882 A | 7/1998 | Lerman et al. | |
| 5,813,999 A | 9/1998 | Ayers et al. | 604/890.1 |
| 5,830,236 A | 11/1998 | Mouchawar et al. | 607/5 |
| 5,906,633 A | 5/1999 | Mouchawar et al. | 607/5 |
| 5,987,354 A * | 11/1999 | Cooper et al. | 607/5 |
| 6,091,989 A | 7/2000 | Swerdlow et al. | 607/5 |
| 6,298,266 B1 | 10/2001 | Rubin et al. | 607/5 |
| 6,327,500 B1 | 12/2001 | Cooper et al. | 607/5 |
| 6,438,418 B1 | 8/2002 | Swerdlow et al. | 607/5 |
| 6,484,056 B2 | 11/2002 | Fisher et al. | 607/5 |
| 6,519,493 B1 | 2/2003 | Florio et al. | 607/6 |
| 6,697,670 B2 | 2/2004 | Chomenky et al. | |
| 6,714,818 B1 | 3/2004 | Fishler et al. | 607/5 |

(Continued)

FOREIGN PATENT DOCUMENTS

EP   0 780 140 A2   6/1997

(Continued)

OTHER PUBLICATIONS

Ganesh Manoharan MD et al., "Novel Passive Implantable Atrial Defibrillator Using Transcutaneous Radiofrequency Energy Transmission Successfully Cardioverts Atrial Fibrillation," *Circulation*, Sep. 2003; vol. 108, No. 11, pp. 1382-1388.

(Continued)

*Primary Examiner*—Kennedy J Schaetzle

(57) ABSTRACT

Techniques are provided for generating plateau-shaped cardioversion shocks having reduced lead edge voltages. The reduced leading edge voltages are provided primarily to reduce the likelihood that any cardiac pain receptors will fire twice during a single cardioversion shock. Other techniques described herein relate to the generation of plateau-shaped shocks without reduced leading edge voltages. Still other techniques pertain to the generation of pre-pulse pain inhibition (PPI) pulses, particularly PPI pulses having chevron-shaped waveforms.

18 Claims, 16 Drawing Sheets

U.S. PATENT DOCUMENTS

| | | | |
|---|---|---|---|
| 6,745,073 B1 | 6/2004 | Kroll | 607/4 |
| 6,763,266 B1 | 7/2004 | Kroll | 607/7 |
| 6,772,007 B1 | 8/2004 | Kroll | 607/7 |
| 6,954,669 B1 | 10/2005 | Fishler et al. | 607/5 |
| 7,155,286 B1 | 12/2006 | Kroll et al. | |
| 7,231,255 B1 | 6/2007 | Kroll et al. | |
| 2004/0044370 A1 | 3/2004 | Benser et al. | 607/5 |
| 2004/0116967 A1 | 6/2004 | DeGroot et al. | 607/5 |
| 2004/0220628 A1 | 11/2004 | Wagner | |

FOREIGN PATENT DOCUMENTS

| | | |
|---|---|---|
| EP | 0 780 140 A3 | 10/1998 |
| WO | WO 93/20892 | 10/1993 |
| WO | WO 99/19021 | 4/1999 |
| WO | WO 99/51300 A2 | 10/1999 |
| WO | WO 99/51300 A3 | 10/1999 |
| WO | WO 01/021255 A1 | 3/2001 |
| WO | WO 2004/050183 A1 | 6/2004 |

OTHER PUBLICATIONS

Matthew G. Fishler, Member, IEEE, *"Theoretical Predictions of the Optimal Monophasic and Biphasic Defibrillation Waveshapes,"* *IEEE Trans Biomed Eng.*, Jan. 2000; vol. 47, No. 1, pp. 59-67.

Notice of Allowance, mailed Sep. 20, 2006: Related U.S. Appl. No. 10/855,654.

NonFinal Office Action, mailed Sep. 26, 2006: Related U.S. Appl. No. 10/855,840.

Notice of Allowance, mailed Mar. 8, 2007: Related U.S. Appl. No. 10/855,840.

NonFinal Office Action, mailed Oct. 4, 2007: Related U.S. Appl. No. 11/005,976.

Final Office Action, mailed Mar. 20, 2008: Related U.S. Appl. No. 11/005,976.

Advisory Action, mailed Jun. 18, 2008: Related U.S. Appl. No. 11/005,976.

* cited by examiner

SYSTEM AND METHOD FOR REDUCING PAIN ASSOCIATED WITH CARDIOVERSION SHOCKS GENERATED BY IMPLANTABLE CARDIAC STIMULATION DEVICES

RELATED APPLICATION DATA

This application is a continuation-in-part (CIP) of copending U.S. patent application Ser. No. 11/005,976, filed Dec. 6, 2004, entitled "System and Method for Reducing Pain Associated with Cardioversion Shocks Generated By Implantable Cardiac Stimulation Devices By Using Plateau-Shaped Waveforms", which was a continuation-in-part (CIP) of U.S. patent application Ser. No. 10/855,654, filed May 26, 2004, entitled "System and Method for Reducing Pain Associated with Cardioversion Shocks Generated By Implantable Cardiac Stimulation Devices", now U.S. Pat. No. 7,155,286, which is related to U.S. patent application Ser. No. 10/855,840, filed May 26, 2004, entitled "System and Method for Reducing Pain Associated with Cardioversion Shocks Generated by Implantable Cardiac Stimulation Devices", now U.S. Pat. No. 7,231,255.

FIELD OF THE INVENTION

The invention generally relates to implantable cardiac stimulation devices such implantable cardioverter/defibrillators (ICDs) and, in particular, to techniques for generating cardioversion shocks modified to reduce pain associated with the shock.

BACKGROUND OF THE INVENTION

Atrial fibrillation ("AF") is a cardiac arrhythmia wherein the atria beat chaotically, thereby providing generally poor conduction of blood into the ventricles of the heart and hence reducing the flow of blood throughout the body. AF has been shown to lead to long-term health problems such as increased risk of thrombolytic stroke. AF can also cause reduced cardiac efficiency, irregular ventricular rhythm and unpleasant symptoms such as palpitations and shortness of breath. In some cases, AF can trigger ventricular fibrillation (VF) wherein the ventricles of the heart beat chaotically thereby providing little or no blood flow to the brain and other organs. VF, if not terminated, is usually fatal.

Hence, it is highly desirable to terminate AF should it arise and revert the atria to a normal rhythm. The current, most common therapy for atrial fibrillation is the administration of anti-arrhythmic drugs that control atrial and ventricular rates during AF. However, these drugs can actually be proarrhythmic, causing the arrhythmia to worsen. At best, anti-arrhythmic drugs appear to provide short-term therapy. Another technique for terminating AF is to administer an electrical cardioversion shock to the atria of the heart. The cardioversion shock, if successful, terminates the chaotic pulsing of the atria and causes the atria to resume a normal beating pattern. Patients prone to AF may have an ICD implanted therein capable of detecting AF and automatically administering one or more cardioversion shocks to terminate AF. Typically, about two joules of energy is administered within each cardioversion shock at an initial voltage of between 100 to 500 volts (V). The duration of the pulse is usually between 5-15 milliseconds (ms) and is a descending voltage capacitive discharge waveform. State of the art ICDs are also capable of detecting a wide variety of other heart arrhythmias, such as VF, and for administering appropriate therapy as well. For VF, the ICD administers a much stronger cardioversion shock (referred to as a defibrillation shock) directly to the ventricles of the heart. The defibrillation shock typically has at least ten to twelve joules of electrical energy. Note that, herein, "cardioversion" generally refers to the delivery of any electrical shock intended to synchronize action potentials of myocardial cells within the heart to terminate arrhythmias. Defibrillation, herein, refers to a type of cardioversion specifically intended to terminate fibrillation.

Although atrial cardioversion shocks have been found to be effective for terminating AF within many patients, the shocks can be quite painful. One reason is that the patient is typically conscious and alert at the time the shock is administered. In contrast, the much stronger ventricular defibrillation shocks for terminating VF are typically not administered until the patient has lost consciousness and hence the patient may feel only residual chest pain upon being revived. Because AF is not usually immediately life-threatening, painful cardioversion shocks for its treatment are often perceived by patients as being worse than the condition itself and therefore not tolerated. Indeed, anxiety arising from the fear of receiving a painful cardioversion shock may be sufficient to raise the heart rate sufficiently to trigger the shock. As some patients have hundreds of AF episodes per year, techniques for reducing the pain associated with cardioversion shocks are highly desirable. It is also desirable to reduce pain associated with ventricular defibrillation shocks. Although patients receiving ventricular defibrillation shocks are usually unconscious when the shock is delivered, in some cases, such shocks are erroneously delivered while the patient is conscious due to false-positive VF detection, resulting in considerable patient pain.

One method for reducing pain arising from cardioversion shocks involves altering the stimulation waveform of the shock to, for example, reduce or smooth initial voltage peaks. See, for example, U.S. Pat. No. 5,830,236, to Mouchawar et al., entitled "System for Delivering Low Pain Therapeutic Electrical Waveforms to the Heart" and U.S. Pat. No. 5,906,633, also to Mouchawar et al., entitled "System for Delivering Rounded Low Pain Therapeutic Electrical Waveforms to the Heart." Shock smoothing is illustrated by way of FIGS. 1 and 2. FIG. 1 illustrates a conventional cardioversion shock waveform 1 (shown in V) along with a resulting cardiac membrane response 2. Herein, the cardiac membrane response is shown in arbitrary response units for the purposes of comparison. The shock waveform is biphasic, with a peak voltage of the initial (positive) phase at about 100 V and with a peak voltage of the second (negative) phase at about 33 V. The peak of the resulting cardiac membrane response occurs at about 4 ms and is at about 50 response units. Peak voltage of the initial phase is typically regarded as the primary determinant of shock pain; whereas the peak cardiac membrane response is typically regarded as the primary indicator of shock effectiveness. Hence, with the conventional shock waveform of FIG. 1, the effectiveness of the shock is only about 50 cardiac response units; the resulting pain is associated with 100 V.

FIG. 2, in contrast, illustrates a smoothed cardioversion waveform 3 along with a resulting cardiac membrane response 4, shown in the same arbitrary response units of FIG. 1 for comparison purposes. The shock waveform of FIG. 2 is smoothed so as to reduce the peak voltage of the initial phase to about 70 V. The peak voltage of the second (negative) phase remains at about 33 V. The peak of the resulting cardiac membrane response is still about 45 response units. Hence, with the smoothed shock waveform of FIG. 2, the cardioversion shock is almost as effective as with the non-smoothed waveform of FIG. 1; whereas the resulting pain is significantly lower, i.e. the resulting pain is associated with a peak voltage of only about 70 V rather than with a peak voltage of 100 V.

One way to generate the smoothed waveform of FIG. 2 is to start with a higher initial capacitor voltage (about 160 V) than the non-smoothed waveform of FIG. 1 and then use resistive loss to lower the voltage as needed. The capacitor voltage is shown by way of phantom line 5, which decreases exponentially. The capacitor voltage at each point in time must be at least as great as the output pulse being generated at that same point in time. During times when the capacitor voltage is greater than the corresponding output shock voltage, the additional energy is dissipated as heat. Thus, pain reduction is achieved at the expense of consuming somewhat greater energy per shock.

Note that the shock waveforms of FIGS. 1 and 2 both provide a fairly substantial peak voltage for the second (negative) phase as compared to that of the initial phase. For the non-smoothed waveform of FIG. 1, the peak voltage of the second phase is at least about one third that of the initial phase. For the smoothed waveform of FIG. 2, the peak voltage of the second phase is at least about four tenths that of the initial phase. Conventionally, it is believed that the second phase must have a fairly large peak voltage is comparison with that of the initial phase to achieve a suitable defibrillation threshold. In addition, conventionally, it is believed that long duration shock phases are disadvantageous. For example, in the case of FIG. 1, the peak cardiac membrane response is achieved at about 4 ms, although the voltage remains relatively high until the 6 ms point, at which it is finally truncated. Truncation of the first phase of a conventional shock waveform is performed, in large part, to reduce the amount of shock energy delivered after the peak membrane response. In this regard, the smoothed waveform of FIG. 2 has the advantage of achieving peak membrane response just at the end of the initial phase with the voltage of the initial (positive) phase then decreasing promptly before commencement of the second (negative) phase.

Note also that the graphs of FIGS. 1 and 2, and all other graphs provided herein, include stylized representations of the parameters being illustrated. This is done so as to more clearly illustrate pertinent features of those parameters. The graphs should not be construed as illustrating actual clinically-detected parameters.

Thus, smoothed waveforms of the type shown in FIG. 2 can be effective in reducing the resulting pain. It would be desirable, however, to achieve an even greater amount of pain reduction without reducing shock effectiveness. It is to that end that certain aspects of the invention are directed. Moreover, it would also be desirable to provide a relatively simple circuit capable of generating improved shock waveforms and other aspects of the invention are directed to that end.

Another method for reducing pain arising from cardioversion shocks is to deliver a pre-pulse pain inhibition (PPI) pulse prior to the main shock. See, for example, U.S. Pat. No. 6,091,989 to Swerdlow et al., entitled "Method and Apparatus for Reduction of Pain from Electric Shock Therapies." With PPI techniques, a relatively weak stimulus (the PPI pulse) is applied to the patient shortly before a main cardioversion shock. The human pain perception system responds to the weak stimulus in such manner that the pain associated with the subsequent main cardioversion shock is reduced or otherwise inhibited. PPI techniques typically employ either a single relatively long, low-voltage PPI pulse or a single relatively short, high-voltage PPI pulse. The long, low-voltage PPI pulse is usually delivered at about 12-20 V. The shorter, high-voltage PPI pulse is usually delivered at the voltage of the subsequent main cardioversion shock. Each has its respective advantages and disadvantages.

Conventional low-voltage and high-voltage PPI pulses are illustrated by way of the timing diagrams of FIG. 3, which show a low-voltage PPI pulse 6 followed by a high-voltage main cardioversion shock 7 and which also show a much shorter high-voltage PPI pulse 8 followed also by a main shock 9. All waveforms of FIG. 3 are monophasic, though biphasic waveforms may instead be employed. None of the waveforms has been smoothed. The exemplary low-voltage PPI pulse and its subsequent main shock are of substantially equal duration (typically about 1-10 ms) but the PPI pulse has an initial peak voltage of only about 20 V whereas the main shock has an initial peak voltage of about 100 V. The exemplary high-voltage PPI pulse is much shorter than its subsequent main shock (e.g., as short as 0.1 ms as opposed to 1-10 ms) but is of equal voltage (again about 100 V). In each case, the PPI pulse is provided to reduce the pain perceived by the patient during the subsequent main cardioversion shock. The time scale of FIG. 3 is arbitrary but, typically, PPI pulses are delivered 30-500 ms prior to the main cardioversion shock.

A significant advantage of generating a short, high-voltage PPI pulse at the same voltage as the main shock is that only a single shocking capacitor is required, precharged to the main shock voltage. To instead deliver a PPI pulse at a low-voltage followed by a main shock at a much higher voltage, two shocking capacitors are usually required—one precharged to the low-voltage and the other precharged to the high-voltage. However, high-voltage PPI pulses can be painful in and of themselves thus reducing their effectiveness in overall pain reduction. Hence, low-voltage PPI pulses are typically preferred despite the need for an extra shocking capacitor. In this regard, note that capacitors used for generating conventional pacing pulses ordinarily cannot be employed to also generate low-voltage PPI pulses, which typically require a somewhat higher voltage than the pacing pulses.

One technique for delivering high-voltage PPI pulses that are not painful in and of themselves is to utilize extremely short duration "sliver" pulses, which are typically only about 25-50 microseconds ($\mu$s) in duration. The sliver pulses are nevertheless sufficient to provide pain inhibition. Preferably, the high-voltage PPI sliver pulses are delivered between electrodes implanted within the heart, such as between a right ventricular (RV) coil and a superior vena cava (SVC) coil, so that high-voltage can be used without risk of significant pain arising from the PPI pulse itself. In particular, pain is reduced by generating the PPI pulse away from the device can or housing. Pulses instead generated using the device can as a return electrode may stimulate sensitive skin nerves and sensitive alpha motor neurons in the pectorals. The subsequent main cardioversion shock is preferably delivered using widely spaced electrodes, such as between the SVC coil and the housing of the implanted device, to ensure maximum likelihood of success. Sliver pulses are discussed in U.S. patent application Ser. No. 10/428,222 of Kroll et al., entitled "System and Method for Generating Pain Inhibition Pulses Using an Implantable Cardiac Stimulation Device", filed Apr. 30, 2003, which is incorporated by reference herein.

Still further improvements were set forth in U.S. patent application Ser. Nos. 10/855,654 and 11/005,976, cited above. These improvements, which are also described hereinbelow, pertain to the use of relatively low-voltage PPI pulses with chevron-shaped waveforms and relatively high-voltage main shocks having plateau-shaped waveforms. By employing plateau-shaped waveforms for the main shocks, a greater cardiac membrane response can be achieved at an equivalent peak voltage as compared to conventional shock waveforms.

As peak voltage is a significant contributor to pain caused by cardioversion shocks, the use of a plateau-shaped waveform helps achieve pain reduction without significant loss of shock effectiveness. Moreover, by employing chevron-shaped PPI pulses in combination with plateau-shaped main shocks, a relatively simple shocking circuit having a single high-voltage shocking capacitor may be used, thus eliminating the need for both low-voltage PPI capacitors and higher voltage main shock capacitors.

Although the aforementioned techniques are effective, there are still further opportunities for pain reduction. The plateau-based techniques summarized above primarily operate to reduce pain by reducing the peak voltage of the shock. For relatively short duration waveforms, this is typically sufficient. However, for longer duration waveforms—particularly waveforms having a first phase longer than 10 ms—it appears that pain receptors refire. That is, pain receptors initially triggered at the beginning of the first phase of the shock appear to refire before the first phase is complete. This results in somewhat greater perceived pain than would otherwise be expected when using a plateau-shaped waveform. The present invention is primarily directed to techniques for addressing this issue to achieve a still further reduction in pain.

SUMMARY

In accordance with one illustrative embodiment, a cardioversion technique is provided wherein a therapeutic shock having a plateau-shaped waveform with a reduced leading edge voltage is generated and then applied to cardiac tissue of the patient. By employing a plateau-shaped waveform with a reduced leading edge, pain reduction can be achieved as compared to plateau-shaped waveforms without a reduced leading edge, at least for longer shocks (e.g. shocks 10 ms or longer.) In particular, the reduced leading edge voltage helps prevent at least some pain receptors from firing twice during the same shock. In this regard, the reduced leading edge voltage helps ensure that pain receptors do not begin firing until somewhat later during the shock. As a result, in many cases, the higher voltage plateau portion of the shock has already been completed before the pain receptors are capable of refiring. At that time, the shock voltage is no longer high enough to trigger the pain receptors and so the receptors do not refire. In this manner, pain receptors typically fire only once during the shock, if at all. Moreover, although a reduction in the leading edge voltage can thereby reduce perceived pain, the reduction does not significantly reduce the therapeutic efficacy of the shock. In other words, pain reduction may be achieved without any loss of cardioversion efficacy.

Preferably, the therapeutic shock is a biphasic shock having first and second phases wherein both phases have plateau portions. However, only the first phase exhibits the reduced leading edge voltage. The second phase has a peak amplitude substantially less than that of the first phase such that the second phase does not contribute to perceived pain. In one example, the first phase has an overall duration of 8-15 ms and the second phase has a duration of only 2-5 ms. The leading edge voltage of the first phase is 30% to 70% of the plateau voltage (i.e. peak voltage) of the first phase. Preferably, the voltage increases gradually from the leading edge voltage to the higher plateau voltage. In one specific example, the gradual increase is in voltage is asymptotic to the plateau voltage. In another example, the increase in voltage is exponential to the plateau voltage. Also preferably, the gradually increasing voltage does not reach the plateau voltage until about halfway through the first phase of the shock. Hence, for a shock with a 10 ms first phase, the shock voltage does not reach the peak, plateau voltage until 5 ms has elapsed, leaving only an additional 5 ms at the plateau voltage. With appropriate setting of the amplitude of the plateau voltage, it can thereby be substantially assured that any pain receptors triggered during the shock will not have an opportunity refire, thus achieving the aforementioned reduction in perceived pain. The appropriate amplitude for the voltage of the plateau portion of the shock depends upon the particular patient and can be determined by the clinician following device implant.

The techniques of the invention are advantageously employed to generate cardioversion shocks for delivering in response to AF but may also be used to deliver other types of therapeutic shocks, such as defibrillation shocks.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

An overview of an implantable device configured to implement the invention is first provided with reference to FIGS. 4-5, then the techniques and circuits of the invention are described in greater detail with reference to FIGS. 6-18.

Overview of Implantable Device

Figure 4:
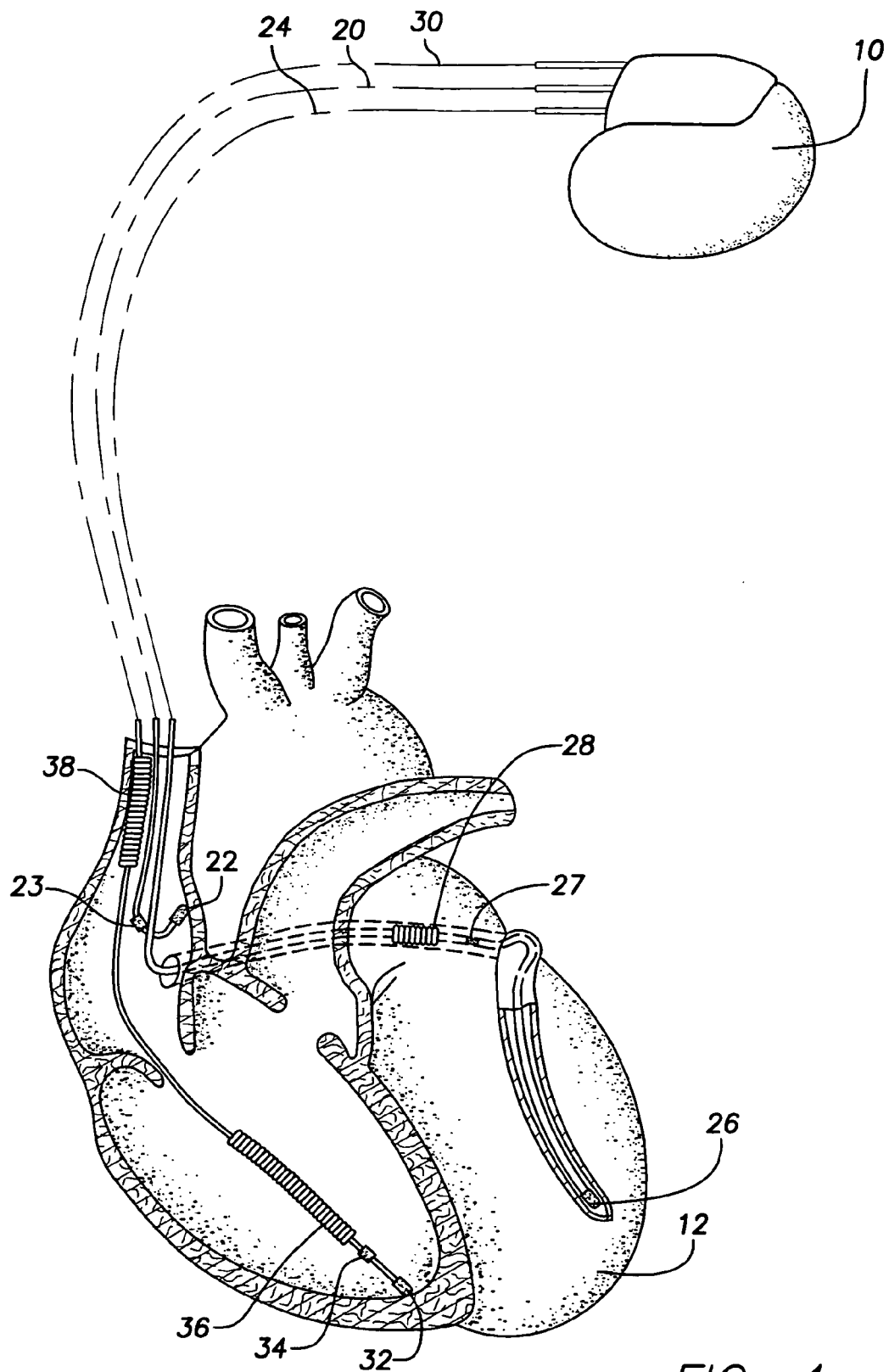
FIG. 4 is a simplified diagram illustrating an implantable stimulation device configured in accordance with the invention in electrical communication with at least three leads implanted into the heart of a patient for delivering multi-chamber stimulation and cardioversion therapy.

FIG. 4 illustrates a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular RV coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle.

Figure 5:
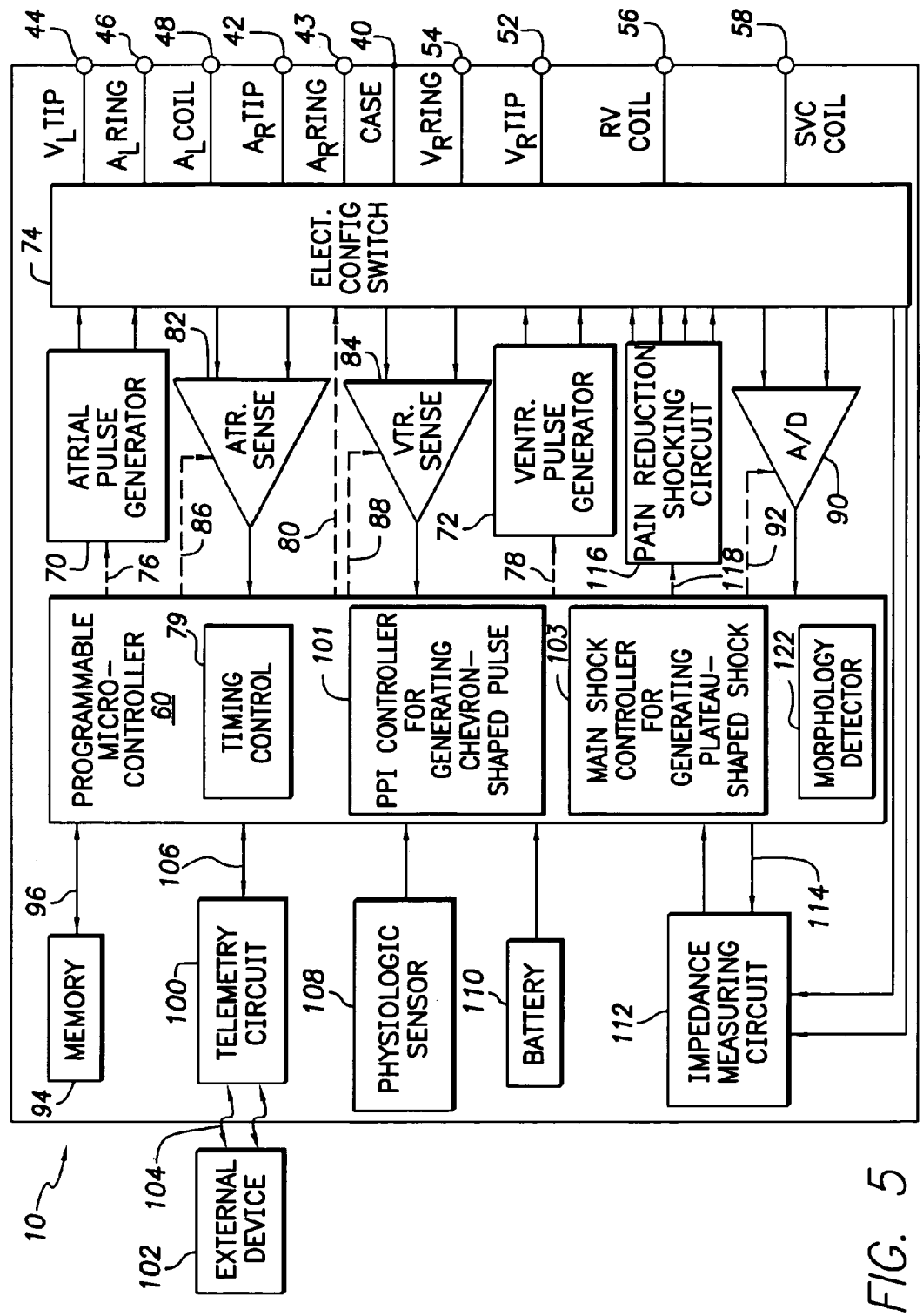
FIG. 5 is a functional block diagram of the implantable cardiac stimulation device of FIG. 4 illustrating basic elements of the stimulation device including components for controlling delivery of the improved plateau-shaped main shocks and the improved chevron-shaped PPI pulses.

As illustrated in FIG. 5, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 5, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. The connector also includes a right atrial ring terminal ($A_R$ RING) 43 adapted for connection to the atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 5, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes for different PPI pulses and main shocking pulses to enable the PPI pulses and shocking pulses to be delivered using different sets of electrodes.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The stimulation device additionally includes a battery or other power supply 110, which provides operating power to all of the circuits shown in FIG. 5. For the stimulation device 10, which employs shocking therapy, the battery 110 is capable of operating at low current drains for long periods of time, and then is capable of providing high-current pulses (for capacitor charging) when the patient requires a shock pulse. The battery 110 also has a predictable discharge characteristic so that elective replacement time can be detected. For example, the device 10 may employ lithium/silver vanadium oxide batteries. As further shown in FIG. 5, the device 10 is shown as having an impedance measuring circuit 112 that is enabled by the microcontroller 60 via a control signal 114.

To deliver cardioversion or defibrillation therapy, device 10 detects the occurrence of an arrhythmia of the type requiring such therapy, and automatically applies an appropriate electrical shock to the heart to terminate the arrhythmia. To this end, the microcontroller 60 further controls a pain reduction shocking circuit 116 by way of a control signal 118. The shocking circuit 116 generates shocking pulses of low (e.g., up to 0.5 joules), moderate (e.g., 0.5-10 joules) or high energy (e.g., 11 to 40 joules), as controlled by the microcontroller 60. Such shocking pulses are applied to the heart of the patient through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks for treatment of AF are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Pain reduction shocking circuit 116 also generates one or more chevron-shaped PPI pulses prior to a plateau-shaped cardioversion shock so as to reduce patient pain and hence is referred to herein as a pain reduction shocking circuit. The chevron-shaped PPI pulses are generated under the control of a PPI controller 101 within the microcontroller, i.e. controller 101 controls shocking circuit 116 to generate the PPI pulses and controls switch 74 to route the PPI pulses to the heart of the patient via selected combinations of electrodes. The plateau-shaped cardioversion shocks are generated under the control of a main shock controller 103 of the microcontroller, i.e. controller 103 controls shocking circuit 116 to generate the main shock and controls switch 74 to route the main shock to the heart of the patient via a potentially different combinations of electrodes. The operation of PPI pulse controller 101 and main shock controller 103 in combination with shocking circuit 116 and switch 74 is described below. Although shown as being part of the microcontroller, the PPI controller and the main shock controller may instead be implemented as components separate from the microcontroller.

Referring to the remaining figures, flow charts and other drawings provide an overview of the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Figure 6:
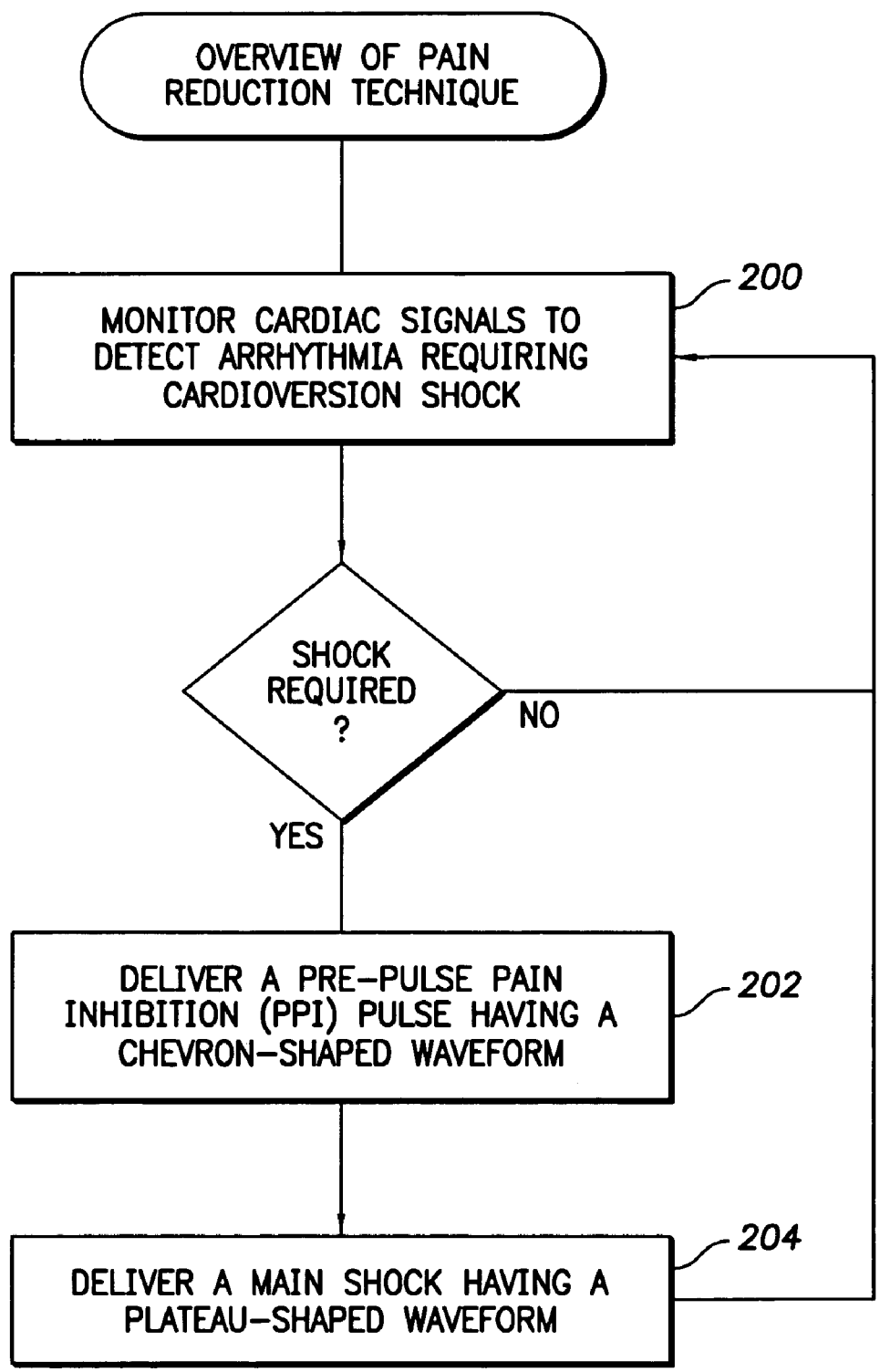
FIG. 6 is a flow chart providing an overview of the shock therapy technique of the invention, which provides a chevron-shaped PPI pulse followed by a plateau-shaped main cardioversion shock.

Pain Reduction Technique Employing Chevron-Shaped PPI Pulses and Plateau-Shaped Main Shocks FIG. 6 illustrates operations performed by the implanted device of FIGS. 4-5 for use in reducing pain associated with cardioversion shocks applied to terminate AF. Similar steps may be performed to reduce pain associated with defibrillation shocks applied to terminate ventricular arrhythmias. Initially, at step 200, the implanted device inputs electrical cardiac signals from the leads illustrated in FIG. 4 and processes the signals to detect the onset of an arrhythmia requiring cardioversion, such as AF. In one implementation, to detect AF, the device tracks the atrial rate based on intrinsic P-waves and, if the atrial rate exceeds an AF detection threshold (AFDT), AF is presumed. In any case, if cardioversion is required, the implanted device then delivers one or more low-voltage PPI pulses each having a chevron-shaped waveform, at step 202. The low-voltage pulses are preferably delivered between electrodes within the heart and the device housing. Thereafter, a main shock having a plateau-shaped waveform is delivered, at step 204. The high-voltage main shock is preferably delivered between fairly closely adjacent electrodes implanted within the heart (such as between RV coil electrode 36 and SVC coil electrode 38 of FIG. 4) so as to concentrate shock energy in the cardiac tissue. The pulses generated by steps 202-204 are graphically illustrated within FIG. 7, which will be described in greater detail below. The generation of the PPI pulses is entirely optional. Alternatively, only the plateau-shaped main shock may be generated and delivered, without any PPI.

Following delivery of the main cardioversion shock, processing returns to step 200 for further monitoring of the electrical cardiac signals to determine if the arrhythmia was properly terminated. If not, the PPI pulses are delivered yet again before a second cardioversion shock is delivered. Although not shown in FIG. 6, for AF, if several cardioversion shocks fail to defibrillate the atria, the implantable device may suspend further delivery of cardioversion shocks to permit the patient to seek medical attention. For VF, defibrillation shocks are repeatedly applied until VF is terminated, usually up to a maximum of six total shocks. In addition, although not shown, during step 200, overdrive pacing techniques may be employed to help prevent the onset of AF or VF. A particularly effective overdrive pacing technique for the atria, referred to as dynamic atrial overdrive (DAO) pacing, is described in U.S. Pat. No. 6,519,493 to Florio et al. A technique for providing multiple-tiered cardioversion and DAO therapy is described in U.S. patent application Ser. No. 10/374,835, of Kroll, entitled "System and Method for Providing Cardioversion Therapy and Overdrive Pacing Using an Implantable Cardiac Stimulation Device", filed Feb. 25, 2003. The techniques described therein, modified as needed, may be used in conjunction with the techniques of the present invention.

Figure 7:
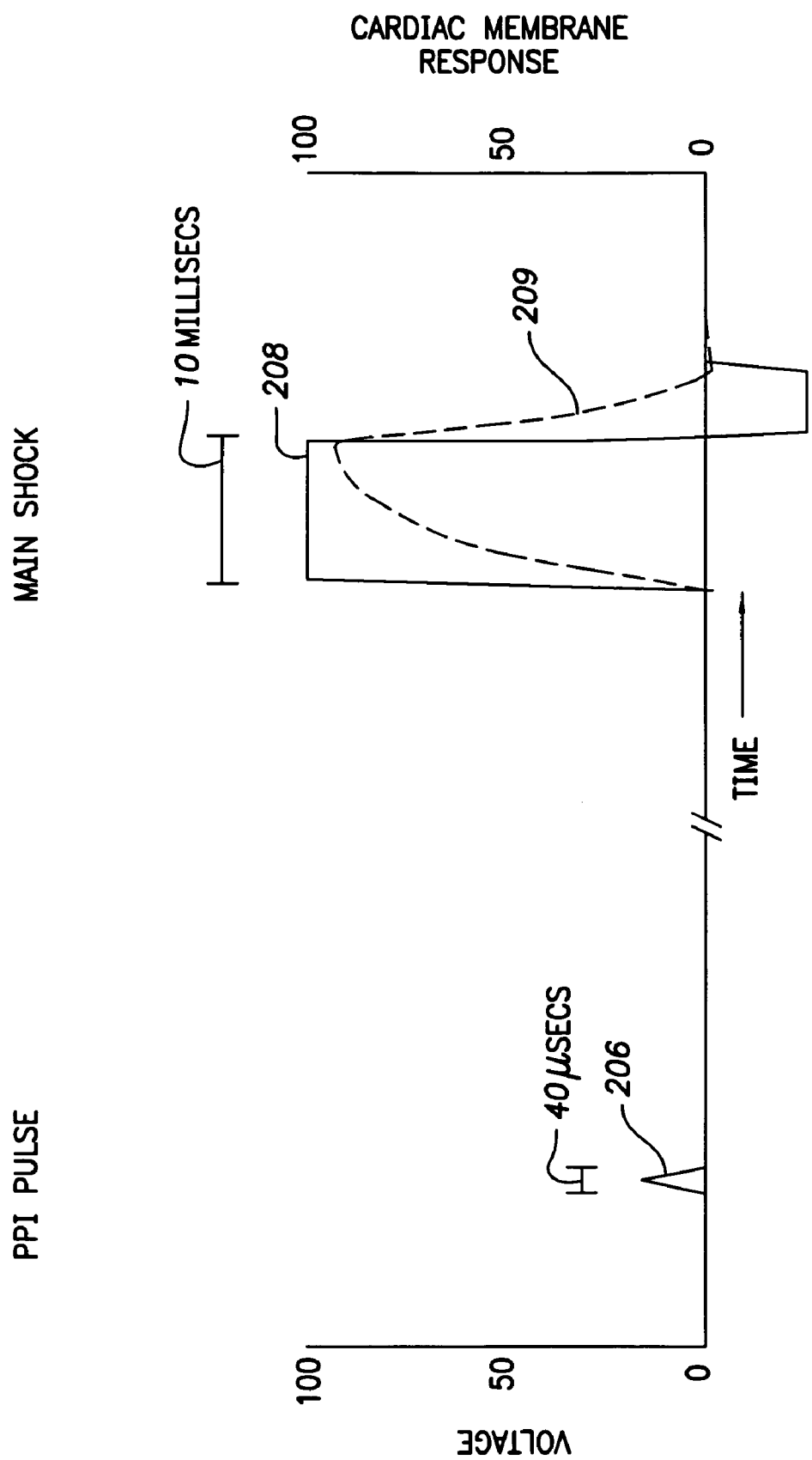
FIG. 7 is a graph illustrating exemplary chevron-shaped PPI pulse followed by an exemplary plateau-shaped main cardioversion shock generated using the technique of FIG. 6.

The chevron-shaped PPI pulse and the subsequent plateau-shaped main shock are shown in FIG. 7. Briefly, chevron-shaped PPI pulse 206 is an extremely short duration sliver pulse lasting only about 40 μs. Plateau-shaped main shock 208 is a biphasic shock having an overall duration, in this example, of about 15 ms. Note that the horizontal time axis of FIG. 7 is not shown to scale due to great differences in pulse duration. In actuality, the 40 μs PPI pulse is 250 times shorter in duration than the plateau-shaped main shock. Instead, within FIG. 7, the horizontal time axis is shown as a "broken" axis to emphasize that the duration of the pulses is not to scale and to further emphasize that the time interval between the pulses is also not to scale. The PPI pulse has a peak voltage of only about 25 V whereas the main chevron plateau-shaped main shock has a peak voltage of about 100 V. The interval between the PPI pulse and main shock is programmable and may be set, for example, in the range of 30 to 500 ms. 80 ms is fairly typical. The duration may depend, for example, on the individual. The delivery of the main shock (and by implication the preceding PPI pulse) are also timed relative to ongoing electrical cardiac signals, in accordance with otherwise conventional techniques, so as to reduce the likelihood that either might be pro-arrhythmic and in particular to avoid triggering VF.

PPI pulse 206 serves to reduce the amount of pain perceived by the patient during the main cardioversion shock by distracting the brain. When the main shock sensation reaches the brain it is busy trying to form a perception of the PP pulse and is not able to fully "appreciate" the pain of the main shock. Volunteers have described the sensation as converting an otherwise extremely sharp pain into a much duller but longer pain. Since a relatively low-voltage is employed for the PPI pulse (only about 25 V), it can be advantageously delivered using widely spaced apart electrodes, such as between the RV tip electrode and the device housing, so as to provide a large antenna for activating a large number of nerve cells throughout the heart and thorax to achieve significant perception for the brain. The plateau-shaped of the main cardioversion shock also serves to reduce the amount of pain perceived by the patient. With the plateau-shaped waveform, pain reduction is achieved as compared to non-smoothed shocks or shocks smoothed in accordance with the conventional techniques discussed above with reference to FIG. 2, at least for equivalent peak voltages. In particular, a greater cardiac membrane response 209 is achieved at an equivalent peak voltage using the plateau-shaped waveform. Within FIG. 7, the cardiac membrane response is in the same arbitrary response units of FIGS. 1 and 2 for comparison purposes.

Figure 1:
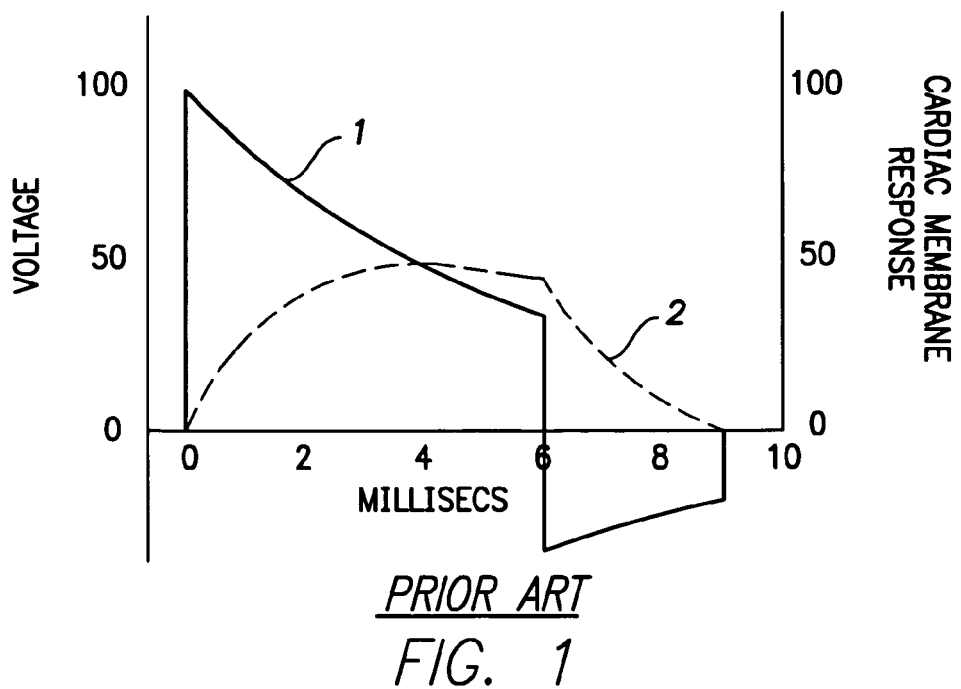
FIG. 1 is a graph illustrating a conventional non-smoothed main cardioversion shock waveform.
Figure 2:
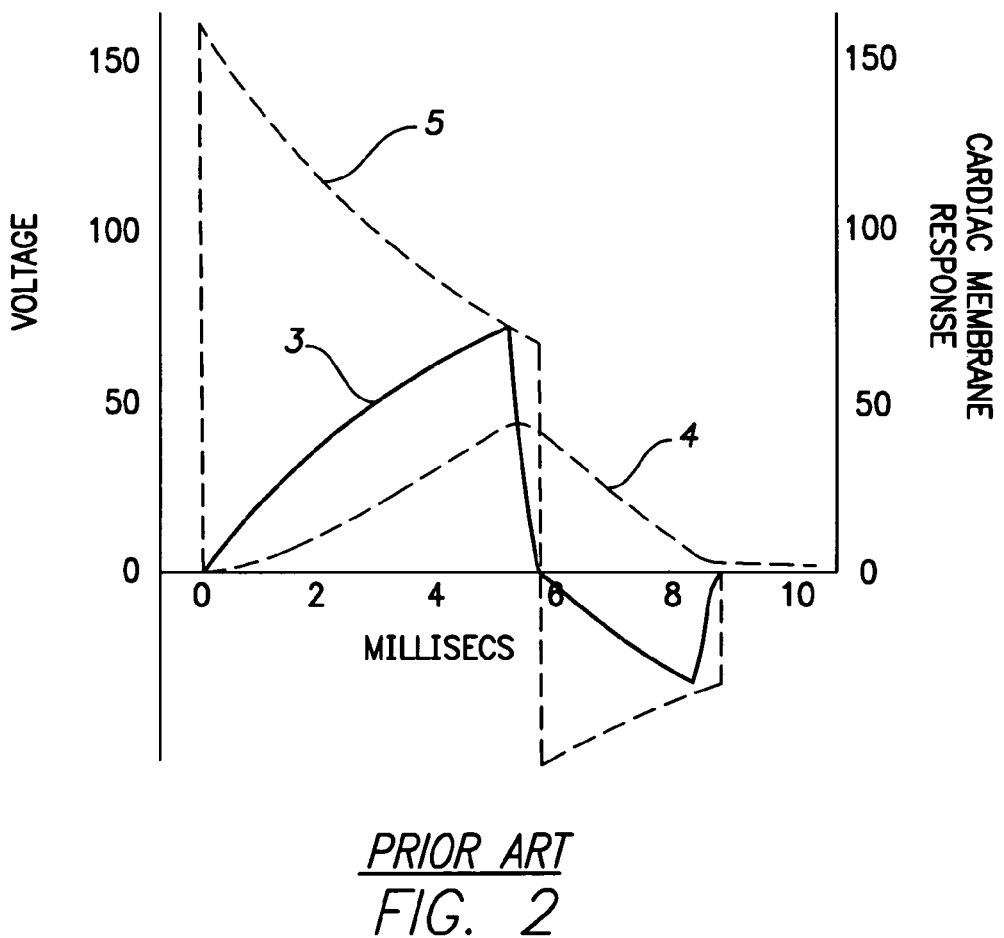
FIG. 2 is a graph illustrating a conventional smoothed main cardioversion shock waveform.

As can be seen, for a peak voltage of 100 V, the cardiac response is over 90 units. In FIG. 1, a cardiac response of only about 50 units is achieved for a non-smoothed waveform at the same peak voltage of 100 V. In FIG. 2, a cardiac response of only about 45 units is achieved for a non-smoothed waveform at a peak voltage of 75 V. Alternatively, when using the smoothed waveform of FIG. 2, a cardiac response of about 60 units is achieved for a peak voltage of about 100 V. Hence, the plateau-shaped waveform can be used to achieve a substantially higher cardiac membrane response at the same peak voltage or can be used to achieve the same cardiac membrane response at a much lower peak voltage. Since peak voltage is a significant contributor to pain experience by the patient, a significant reduction in pain can be achieved by using the plateau-shaped waveform while still achieving the same level of shock effectiveness. In recent human studies, the plateau waveform has been shown to shift a perceived pain threshold by a factor of four, i.e. patients rate a plateau waveform delivered with 4 joules of energy as being no more painful than a conventional descending biphasic shock waveform delivered with 1 joule of energy.

Figure 3:
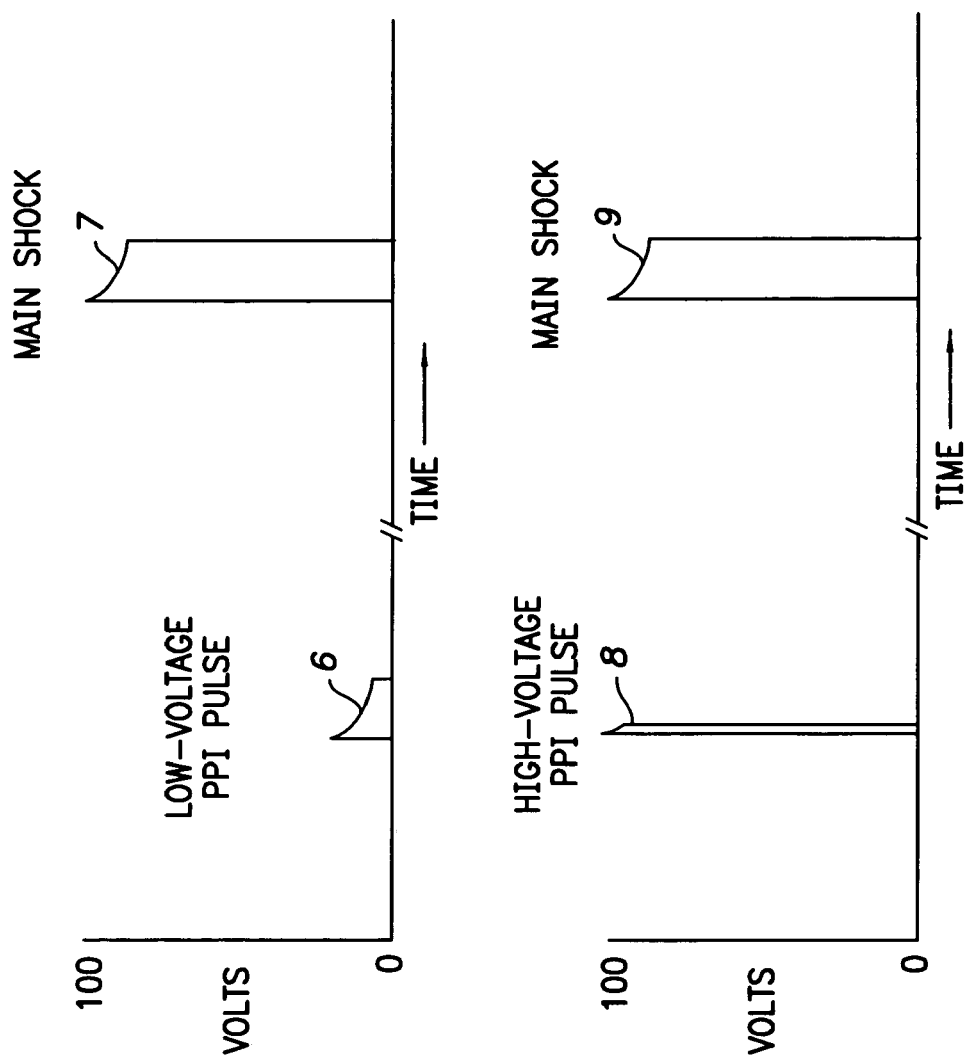
FIG. 3 is a graph illustrating conventional PPI pulses along with non-smoothed main cardioversion shocks.

Thus, both the PPI pulse and the plateau-shape of the main cardioversion shock serve to reduce patient pain. If desired, one technique or the other may be individually employed. In other words, a chevron-shaped PPI pulse may be employed prior to delivery of a conventional non-smoothed main cardioversion shock (such as the shock shown in FIG. 1) or prior to a conventionally smoothed main shock (such as the shock shown in FIG. 2.) Alternatively, conventional PPI pulses (such as those described above with reference to FIG. 3) may be delivered prior to the plateau-shaped main shock of FIG. 7. Preferably, however, both the chevron-shaped PPI pulse and the plateau-shaped main cardioversion shock are employed to achieve a significant enhancement in overall pain reduction for a given level of shock effectiveness. A particular advantage of using both the chevron-shaped PPI pulse and the plateau-shaped main shock is that a single circuit (shown in FIG. 8) may be employed to generate both waveforms using a single shock capacitor. In other words, despite the large voltage difference between the peak of the low-voltage PPI pulse and the peak of the high-voltage main cardioversion shock, a separate low-voltage shock capacitor is not required to generate the chevron-shaped PPI pulse.

Herein the term "chevron-shaped" is used to indicate that the PPI pulse generally has a V-shape or an inverted V-shape. The inverted V-shape is employed if the polarity of the shock is such that its peak voltage is negative rather positive. In the example of FIG. 7, the voltage of the PPI pulse increases linearly from zero (or some other baseline voltage) to a peak voltage, then decreases linearly back to zero (or to the baseline voltage). In other examples, the increase and/or subsequent decrease may only be substantially linear, while still providing a generally V-shaped pulse. In addition, herein, the term "plateau-shaped" is used to indicate that the main pulse has a substantially flat peak. Depending upon the polarity of the shock, the flat peak may have a positive voltage or a negative voltage (relative to zero or relative to some other baseline voltage). In the case of a biphasic shock, the second phase of the shock will have the opposite polarity of the first phase. In the example of FIG. 7, the first phase of the main shock has a voltage that increases linearly during an initial short interval from zero up to a peak voltage, then remains at that peak voltage for a comparatively much longer interval of time, then decreases linearly during another short interval of time back to 0 V. The second phase of the shock has a similar shape, but inverted. In other examples, the increase and/or subsequent decrease may be only substantially linear and/or the peak may be only substantially flat, while still providing a generally plateau-shaped main shock. In the example of FIG. 7, the initial increase in voltage to the peak voltage occurs within about 0.5 ms, the voltage remains at its peak voltage for another 9 ms, then the voltage decreases within about 0.5 ms back to 0 V. These are merely exemplary values.

Figure 8:
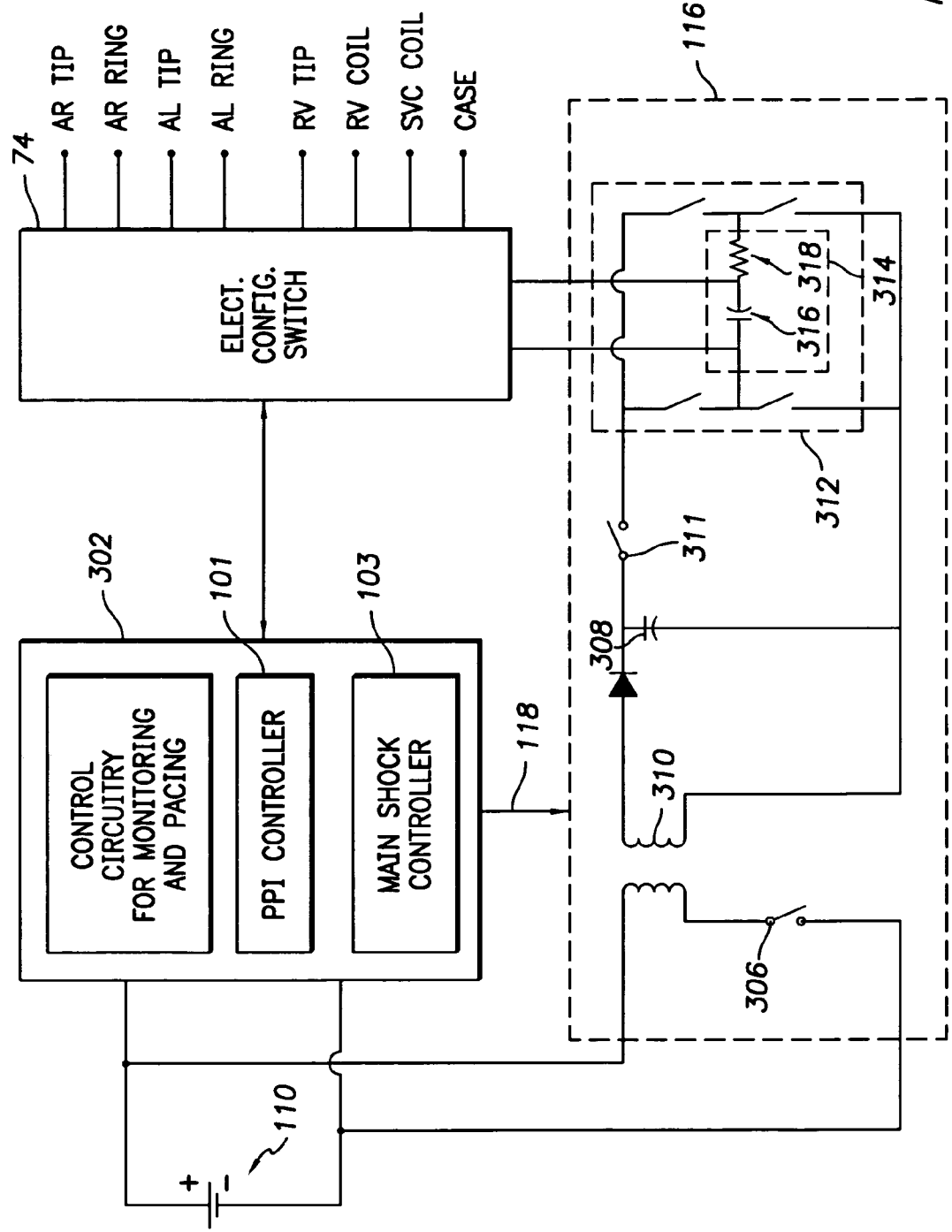
FIG. 8 is a diagram illustrating an exemplary circuit for generating both chevron-shaped PPI pulses and plateau-shaped main cardioversion shocks in accordance with the technique of FIG. 6.

Circuitry for Generating Chevron-Shaped PPI Pulses and Plateau-Shaped Main Shocks Selected internal features of the implanted device of FIG. 5 are illustrated in FIG. 8. Battery 110 provides power for all monitoring and pacing functions, as well as for the generation of the chevron-shaped PPI pulses (under the control of PPI controller 101) and the generation of main cardioversion shocks (under the control of main shock controller 103.) For simplicity, in FIG. 5, a block 302 is used to collectively represent all pacing, monitoring and control circuit components (i.e. all device components shown in FIG. 5, with the exception of switch 74 and pain reduction shocking circuit 116.) Upon detection of an arrhythmia requiring cardioversion by control circuit 302, a control signal is sent along line 118 to pain reduction shocking circuit 116, which causes switch 306 to close to allow current from battery 110 to begin charging a high-voltage capacitor 308 via voltage transformer 310. Once the high-voltage capacitor has reached a predetermined maximum voltage (e.g. 200 V), a chopping switch 311 and an H-bridge switch 312 are controlled (by the signal on line 118) in accordance with a first switching sequence so as to route a small portion of the energy stored within capacitor 308 to electrode configuration switch 74 via a low-pass RC filter 314. More specifically, the chopping switch is held closed while capacitor 308 is discharged through the RC filter for about 20 μs, then the polarity is switched via the H-bridge for another 20 μs. The low-pass RC filter includes a capacitor 316 (which is much smaller than capacitor 308) and a resistor 318, configured as shown. The resistor and capacitor are sized and configured to provide, in this example, a low-pass RC filter time constant of about 100 μs. During the PPI pulse, the effect of the low-pass RC filter is to produce an output pulse having a chevron-shaped waveform. The PPI pulse is routed through switch 74, which operates under the control of the PPI pulse controller, to deliver the PPI pulse to the heart of the patient using, for example, the RV tip electrode with the device case as the return electrode. Note that the chopping switch simply remains closed during the generation of the PPI pulse. The chopping switch is more fully utilized during the generation of the subsequent main shock, as will be described below.

Figure 9:
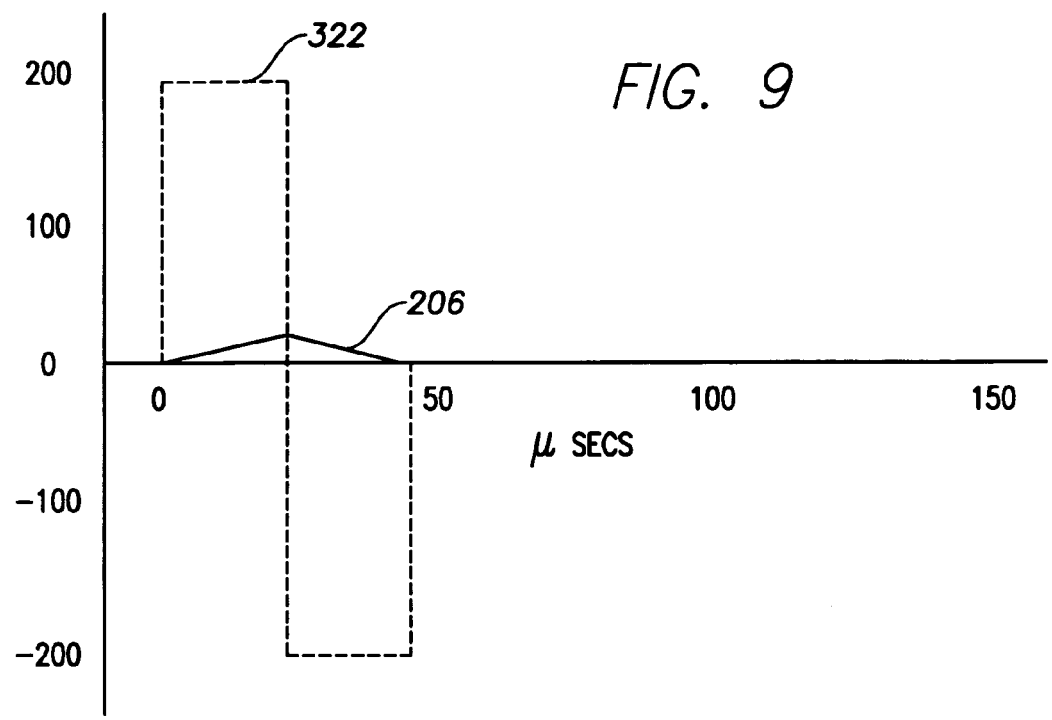
FIG. 9 is a graph particularly illustrating an exemplary chevron-shaped PPI pulse generated using the circuit of FIG. 8.

The resulting chevron-shaped PPI pulse (206) is shown within FIG. 9 along with a corresponding capacitor voltage profile 322, shown in phantom lines. The chevron-shape of the waveform is achieved as a result of the low-pass filter, i.e. the voltage of the PPI pulse waveform increases relatively slowly and substantially linearly due to the presence of the filter, while the voltage input to the filter remains near 200 V. Once the polarity is switched the voltage changes to −200 V, the voltage of the PPI pulse decreases linearly back to zero. As a result, the PPI pulse has an overall duration of 40 μs. Note that the capacitor voltage profile 322 does not show any decrease during either of the 20 μs phases. This is simply because the interval of time shown is so short that no noticeable decrease in voltage occurs. In actuality, a very slight decrease in voltage will occur in the capacitor voltage from its initial peak voltage of 200 V but that amount is not noticeable in the figure.

The 40 μs duration of the PPI pulse is determined primarily by the maximum switching speed of the H-bridge circuit. Current state-of-the-art switching circuits for use within implantable devices have a fastest possible switching speed of about 20 μs and hence a PPI pulse duration of 40 μs is the shortest duration that can easily be achieved at that switching speed. If desired, however, a somewhat slower switching speed, e.g. 25 μs can instead be employed to provide a somewhat longer duration PPI pulse, 50 μs, with a somewhat higher peak voltage. In the preferred embodiment described herein, the quickest possible switching speed is employed to generate the shortest possible PPI pulse so as to ensure a low peak voltage to allow use of the device housing as the return electrode. As noted, this allows for activation of a large number of nerve cells in the chest of the patient so as to achieve reliable perception and hence enhanced pain inhibition. If the duration of the PPI pulse is set to a somewhat longer duration, the peak voltage of the PPI pulse can rise to a point where it is equal to the capacitor voltage. If so, the PPI pulse is preferably delivered between a pair of electrodes implanted in the heart so as to reduce pain associated with the PPI pulse itself. Routine experimentation may be employed to identify a threshold voltage above which the PPI pulse should be delivered between electrodes in the heart. At still longer pulse durations, the PPI pulse will begin to adopt a plateau-shape, with a flat peak at the voltage of the capacitor. Hence, the circuit of the invention is not limited to generating chevron-shaped PPI pulses but is also capable of generating plateau-shaped PPI pulses, should those be desired. With still longer pulse durations, the pain associated with the PPI pulse itself may become too severe (even when delivered between a pair of electrodes in the heart) to be of value as a pain reduction pulse. Again, routine experimentation may be employed to identify a threshold duration beyond which the PPI pulse results in too much pain. At still longer durations, the voltage of the capacitor may decrease during generation of the PPI pulse by an amount requiring that the capacitor be recharged prior to delivery of the main shock.

Returning to FIG. 8, after the PPI pulse is delivered, the shopping switch is opened to prevent further discharge from the capacitor 308. A timer within control circuitry 302 is then activated to track the time interval before delivery of the subsequent main shock. When it is time for delivery of the main shock, the chopping switch and the H-bridge switch are then controlled by main shock controller 103 in accordance with a second switching sequence so as to deliver all or most of the remaining energy stored within capacitor 308 as a plateau-shaped main cardioversion shock. The plateau-shaped main shock is routed through switch 74, which operates under the control of the main shock controller, to deliver the main shock to the heart of the patient between, for example, the SVC coil and the RV coil. Also, note that, for clarity the chopping switch is shown positioned between the main capacitor and the H-bridge. In general, though, it can be positioned at any suitable location within the circuit where it can operate to hold the voltage constant during the plateau phases, such as at a location within the H-bridge. The chopping switch and the H-bridge collectively comprise switching circuitry for selectively discharging the main storage capacitor through the low-pass RC filter for delivery to heart tissue of the patient. Other appropriate circuit configurations may instead be employed consistent with the principles of the invention described herein. Waveform shaping techniques set forth in U.S. patent application Ser. No. 10/687,386, filed Oct. 15, 2003, entitled "Implantable Cardiac Stimulation Device Including an Output Circuit that Provides Arbitrarily Shaped Defibrillation Waveforms", of Moulder et al., may be exploited as well. This application is incorporated by reference herein.

Figure 10:
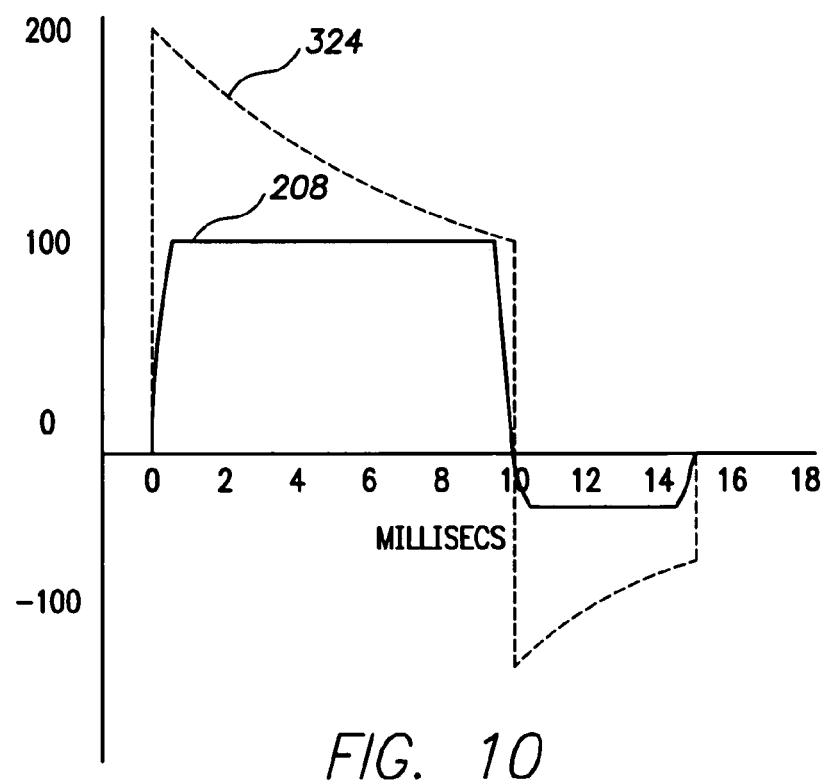
FIG. 10 is a graph particularly illustrating an exemplary plateau-shaped main cardioversion shock generated using the circuit of FIG. 8.

The resulting plateau-shaped PPI pulse (208) is shown within FIG. 10 along with a corresponding capacitor voltage profile 324, shown in phantom lines. As can be seen, the capacitor is again set to an initial voltage of 200 V and is discharged via the H-bridge circuit through the low pass filter with chopping switch 311 closed until the voltage of the output waveform reaches a peak voltage of about 100 V. This takes about 0.5 ms, during which time the increase in voltage of the output waveform is substantially linear and its rate of increase is slowed by the filter. Next, the chopping switch is controlled so as to hold the voltage of the output waveform constant, while the capacitor voltage continues to decrease exponentially. More specifically, the chopping switch is toggled at a high switching rate by the main shock controller 103 so that the output voltage increases very slightly while the chopping switch is closed and decreases very slightly while the chopping switch is open to thereby hold the output voltage substantially constant while the capacitor discharges. In the example, of FIG. 10, the output voltage is held at 100 V for about 9 ms, so as to produce a flat plateau voltage. During this interval of time, the capacitor voltage decreases exponentially down to about 100 V and energy from the capacitor not delivered into the output shock is dissipated as heat. Then, the chopping switch is again held closed and the H-bridge is controlled so as to allow the voltage of the output waveform to drop to 0 V. This takes about 0.5 ms, during which time the decrease in voltage of the output waveform is substantially linear while the capacitor voltage continues to decrease exponentially. The H-bridge is then controlled to switch polarity and the process is repeated to produce the second phase of the main shock, which also has a plateau-shape.

In the example of FIG. 10, the main shock has an overall duration of about 15 ms and its first phase is held at the peak plateau voltage of 100 V for 9 ms. The second phase is held at a peak voltage of about −25 V for a duration of about 2 ms. These are merely exemplary values. Routine experimentation may be employed to identify voltage parameters and waveform shape parameters for maximizing shock effectiveness while minimizing the resulting pain in accordance with the principles of the invention. In general, the duration of the first phase (including the ramp-up and ramp-down "skirt" portions) is preferably in the range of 10-12 ms, as it is believed that a duration within this range serves to minimize both delivered energy DFT while also minimizing voltage DFT for most patients. Delivered energy DFT refers to the minimum energy needed to reliably defibrillate the heart, whereas voltage DFT refers to the minimum voltage need to defibrillate the heart. Routine experimentation may be performed to determine the precise duration for minimizing both delivered energy DFT and voltage DFT for a particular patient, at least within patients in which both minimums can simultaneously be achieved. Alternatively, the duration may be selected so as to minimize voltage DFT, while reducing delivered energy DFT to within 10% of its minimum. Again, routine experimentation may be performed for a particular patient to determine the precise duration for minimizing voltage DFT while also reducing delivered energy DFT to within 10% of its minimum, at least within patients in which that can be achieved.

Although a duration in the range of 10-12 ms is preferred for most patients, a duration in the range of 8-15 ms may be almost as effective. A duration in the range of 7-19 ms may also be useful, as well. However, above 15 ms energy it is believed that energy efficiency suffers. Below 8 ms, it is believed that voltage efficiency decrease and pain perception increases. Also, note that whereas each phase shown has both an initial "ramp-up" skirt and a subsequent "ramp-down", in other implementations, it may be desirable to provide a waveform with either only the ramp-up skirt or only the ramp-down skirt, which may be achieved, for example, using an alternate circuit. Note, also, that the plateau portion of each phase need not be absolutely flat, though flat is preferred. If inclined, an inclination of less than 5% is preferred. Also, if inclined, the inclination is preferably provided so that voltage increases gradually, rather than decreases, at least within the initial phase.

As noted, the second phase has a plateau amplitude of about −25 V and hence has an amplitude only about one quarter that of the first phase. A relative amplitude of less than one third is preferred, with a relative amplitude of one quarter being even more advantageous. A relative amplitude of one fifth may also be suitable. Again, routine experimentation can be performed to identify the optimal ratio of second phase peak amplitude to first phase peak amplitude for particular patients.

Figure 11:
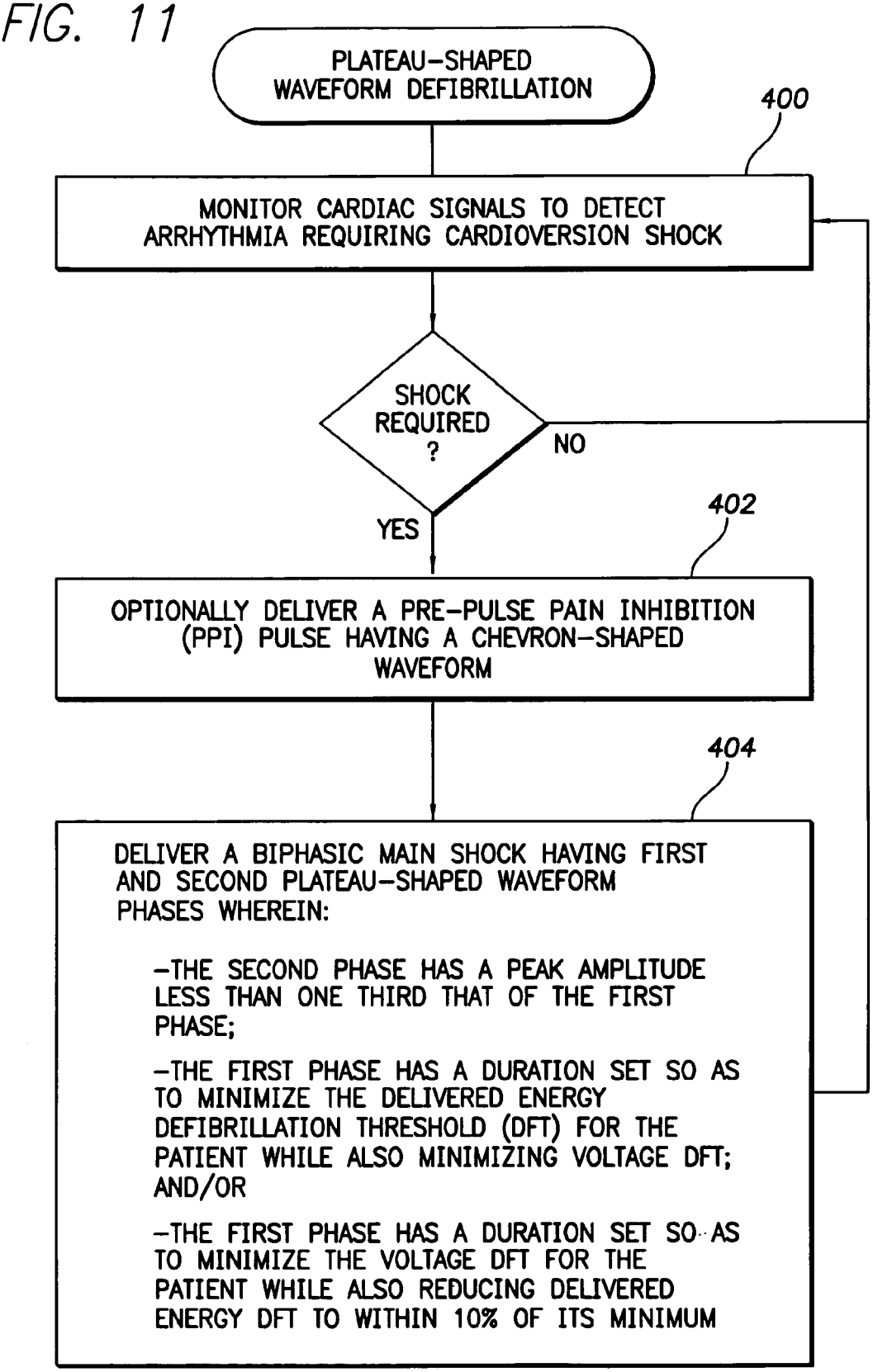
FIG. 11 is a flow chart providing an overview of certain features of the plateau-shaped main cardioversion shock of the invention.

Some of the aforementioned features of the plateau-shaped main shock waveform are summarized in FIG. 11. FIG. 11 is similar to FIG. 6 and only pertinent differences will be discussed. As before, the device monitors cardiac signals to detect an arrhythmia requiring a cardioversion shock, step 400. A chevron-shaped PPI pulse is optionally delivered, at step 402. Then, at step 404, the device generates and delivers a biphasic main shock having first and second plateau-shaped waveform phases. The main shock is configured such that either: the second phase has a peak amplitude less than one third that of the first phase; the first phase has a duration set so as to minimize the delivered energy DFT for the patient while also minimizing voltage DFT; and/or the first phase has a duration set so as to minimize the voltage DFT for the patient while also reducing delivered energy DFT to within 10% of its minimum.

Figure 12:
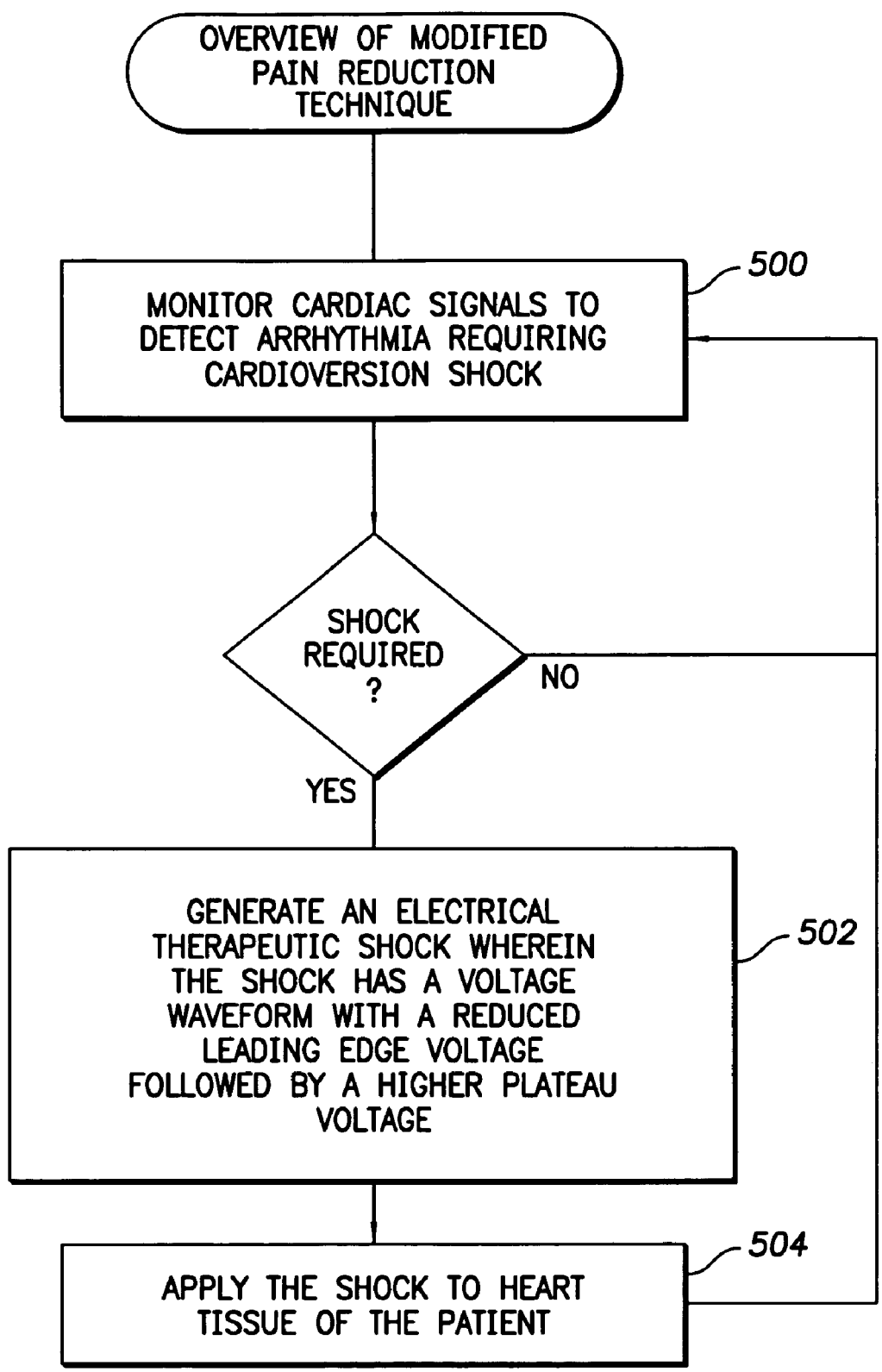
FIG. 12 is a flow chart providing an overview of an alternative shock therapy technique of the invention, which uses a plateau-shaped main cardioversion shock waveform with a reduced leading edge voltage.

Pain Reduction Technique Employing Plateau-Shaped Main Shocks with Reduced Leading Edge Voltages FIG. 12 illustrates an alternative sequence of operations performed by the implanted device of FIGS. 4-5 for use in reducing pain associated with cardioversion shocks applied to terminate AF. Similar steps may be performed to reduce pain associated with defibrillation shocks applied to terminate ventricular arrhythmias. Some of the steps of FIG. 12 are similar to those of FIG. 6 and hence will not be described again in detail. As before, the implanted device inputs electrical cardiac signals, at step 500, and processes the signals to detect the onset of an arrhythmia requiring cardioversion, such as AF. If cardioversion is required, the implanted device then generates, at step 502, a therapeutic, cardioversion "high voltage" shock having a plateau-shaped waveform with a reduced leading edge voltage. The shock is referred to herein as a high voltage shock since it has a peak voltage much higher than pacing pulses and also much higher than the aforementioned chevron-shaped PPI pulses. However, the peak voltage of the shock is nevertheless much lower than conventional cardioversion shocks. For example, the shock generated at step 502 may have a peak voltage of 100 V; whereas conventional cardioversion shocks often have peak voltages of 500 V.

The cardioversion shock is delivered to cardiac tissue at step 504. As with other cardioversion shocks described herein, the shock is preferably delivered between fairly closely adjacent electrodes implanted within the heart so as to concentrate shock energy in the cardiac tissue. Examples of shocks generated at step 502 are graphically illustrated within FIGS. 14-17 and will be described in greater detail below. Although not shown in FIG. 11, the technique may also include the steps of generating and delivering PPI pulses, as described above in connection with FIG. 6. An example wherein a chevron-shaped PPI pulse is delivered prior to a plateau-shaped cardioversion shock with reduced leading edge voltage is illustrated in FIG. 18, discussed below. Following delivery of the cardioversion shock, processing returns to step 500 for further monitoring of the electrical cardiac signals to determine if the arrhythmia was properly terminated. If not, additional cardioversion shocks may be delivered, as discussed above in connection with FIG. 6. In addition, during step 500, overdrive pacing techniques may be employed to help prevent the onset of AF or VF, as also discussed above.

Figure 13:
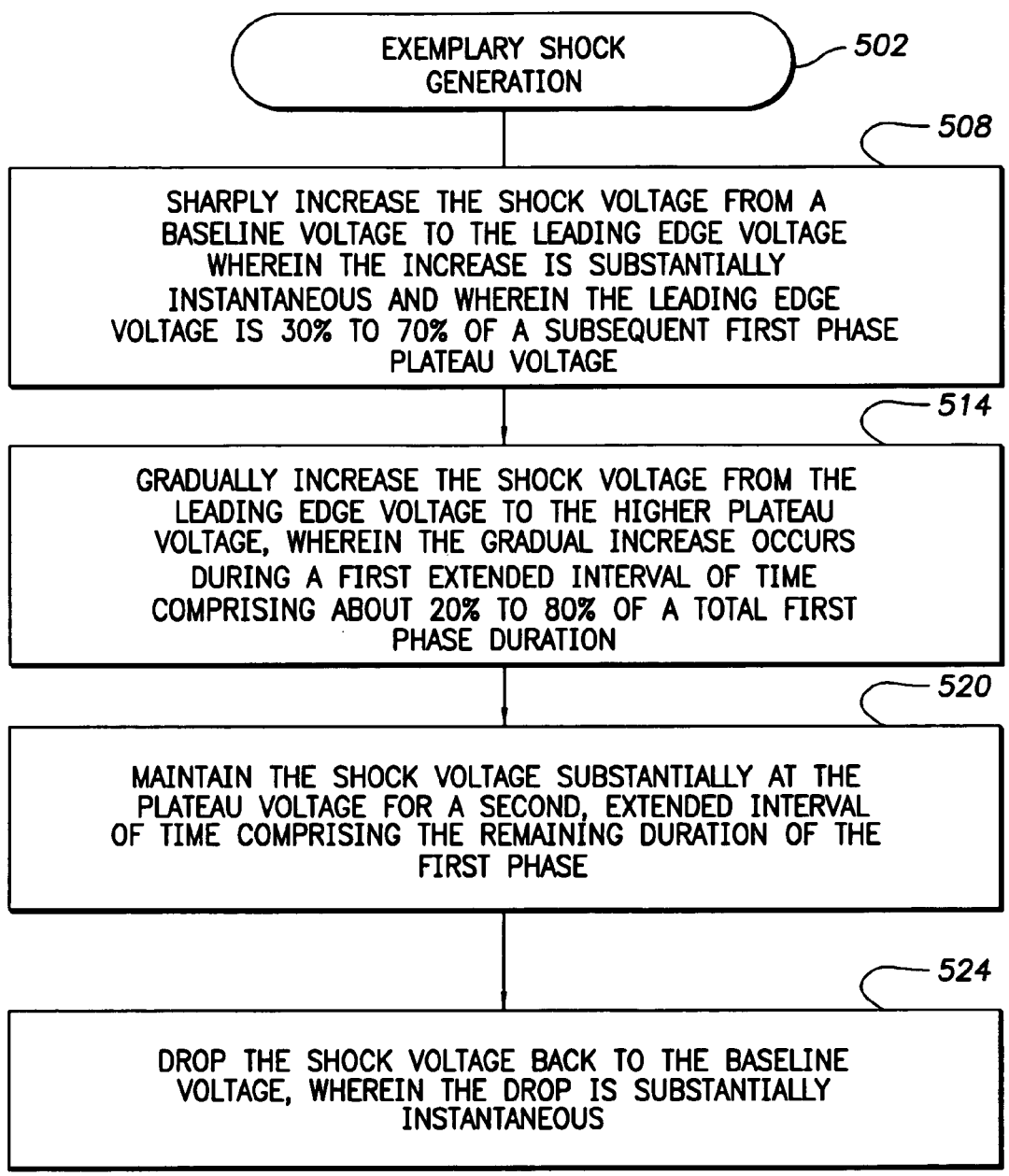
FIG. 13 is a flow chart summarizing steps performed to generate the plateau-shaped shock waveform of FIG. 12.
Figure 14:
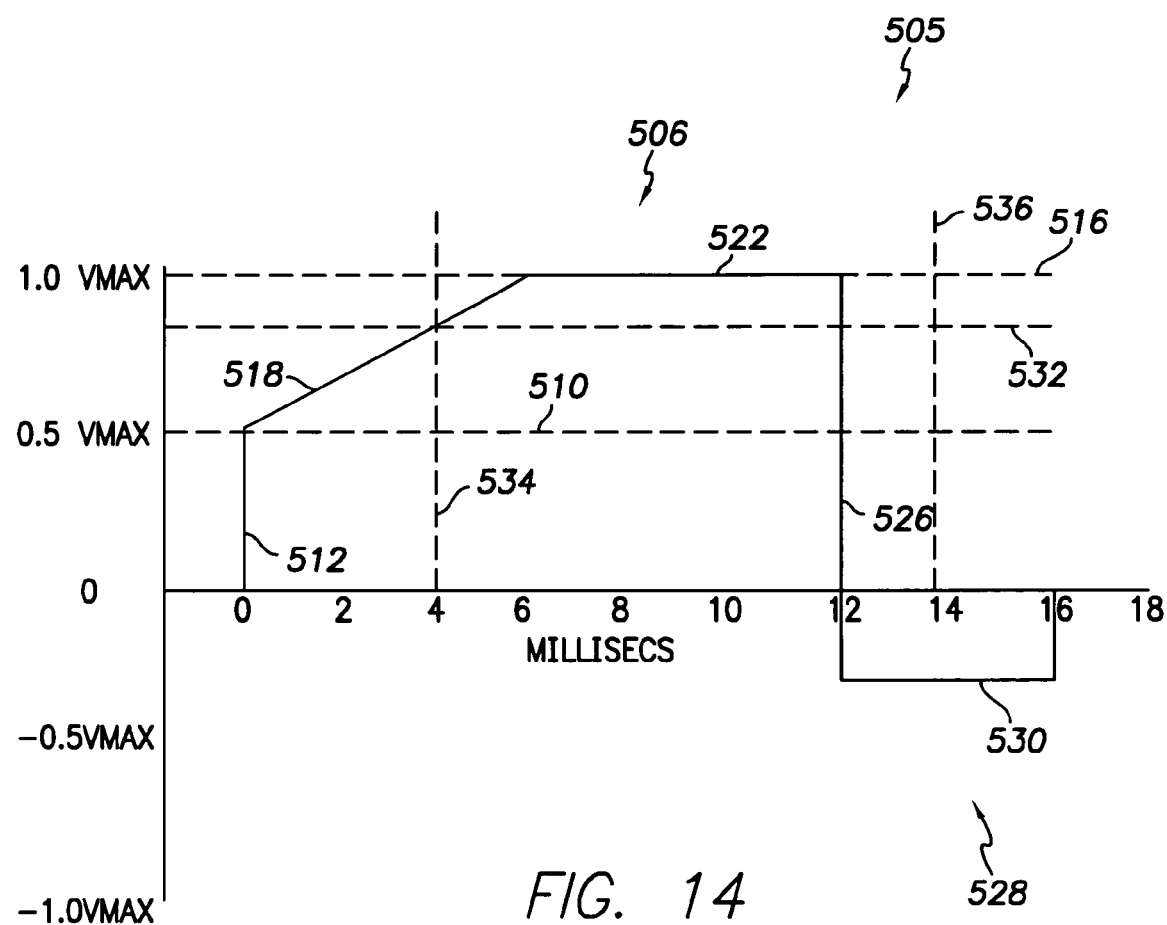
FIG. 14 is a graph illustrating a first exemplary plateau-shaped main cardioversion shock generated using the technique of FIGS. 12 and 13, wherein the shock voltage increases linearly from the leading edge voltage to the higher plateau voltage.

FIG. 13 summarizes sub-steps that may be performed during step 502 of FIG. 12 to generate the cardioversion shock. FIG. 13 will be described in conjunction with FIG. 14, which graphically illustrates an exemplary cardioversion shock 505, having an overall "castle moat" shape. At step 508 of FIG. 13, during a first phase 506 (FIG. 14) of the waveform, the implanted device sharply increases the output, i.e. shock voltage, from a baseline voltage (which may be 0 V) to a leading edge voltage 510, wherein the increase is substantially instantaneous and wherein the leading edge voltage is 30% to 70% of a subsequent peak voltage Vmax (and more preferably about 40% to 60% of Vmax). In the example of FIG. 14, the leading edge voltage is 50% of Vmax. It is tempting to begin a ramp at zero volts thinking that this gradual rise will reduce pain even further. However, with the extremely low voltages, there is no cardiac cell membrane charging. See, Fishler. "Theoretical Predictions of the Optimal Monophasic and Biphasic Defibrillation Waveshapes", IEEE Trans Biomed Eng. 2000 January; 47(1):59-67. Thus, there is only pain with no gain and hence a waste of energy.

For atrial cardioversion, Vmax may be, e.g., 100 V. By "substantially instantaneous" it is meant that the voltage increase is extremely short relative to the overall duration of the first phase shock, typically on the order of only a few microseconds. In FIG. 14, the sharply increasing portion of the shock waveform is denoted by reference numeral 512. Alternatively, the shock voltage can be increased somewhat more slowly. In any case, during step 514 of FIG. 13, the implanted device gradually increases the shock voltage from the leading edge voltage 510 to a higher plateau voltage 516 set equal to Vmax, wherein the gradual increase occurs during a first extended interval of time comprising about 20% to 80% of a total duration of the first phase 506 (and more preferably about 40% to 60% of the duration). Hence, if the duration of the first phase of the cardioversion shock is set to 10 ms, the first interval is 2 ms to 8 ms in duration (and more preferably 4 ms to 6 ms in duration). In FIG. 14, the gradually increasing portion of the shock waveform is denoted by reference numeral 518 and has a duration of about 5 ms. The total duration of the first phase 506 of the waveform is preferably in the range of 8 ms to 15 ms and more optimally in the range of 10 ms to 12 ms.

During step 520 of FIG. 13, the implanted device maintains the shock voltage substantially at the plateau voltage 516 for a second, extended interval of time comprising the remaining duration of the first phase 506 of the cardioversion shock. In FIG. 14, the plateau portion of the shock waveform is denoted by reference numeral 522 and also has a duration of about 5 ms. At step 524 of FIG. 13, the implanted device drops the shock voltage back to the baseline voltage (0 V), wherein the drop is again substantially instantaneous. In FIG. 14, the sharply dropping portion of the shock waveform is denoted by reference numeral 526. Alternatively, the shock voltage can be decreased somewhat more slowly back to the baseline voltage. FIG. 14 also shows a second phase 528 of shock waveform 505, which has a negative plateau 530 with a voltage having an absolute magnitude in the range of 25% to 35% of Vmax. In the example of FIG. 14, the plateau voltage of the second phase of the waveform is about −0.25 Vmax. Unlike the first phase, however, the second phase does not employ a reduced leading edge voltage. Note that the steps for generating the second phase are not specifically shown in FIG. 13. Note also that the polarities of the phases can be reversed, i.e. the first phase may be negative whereas the second phase is positive. Additional phases may additionally be added.

Insofar as pain reduction is concerned, the greatest amount of pain reduction is achieved, as explained above in connection with FIGS. 1-11, by greatly reducing the peak voltage as compared to conventional shocks. For atrial cardioversion, the plateau-shaped shock may have a peak voltage of, e.g., only 100 V as opposed to a conventional shock voltage of 500 V, while achieving the same therapeutic efficacy. The reduced peak voltage helps ensure that most pain receptors do not fire at all during the shock. The reduced leading edge voltage of the technique of FIGS. 12-13 achieves still further pain reduction by helping to ensure that the relatively few pain receptors that do fire despite the lower peak plateau voltage will not fire a second time during the shock. In particular, the reduced leading edge voltage serves to reduce the time interval between when pain receptors fire and the end of the high voltage portion of the shock by an amount sufficient to help prevent the pain receptors from refiring.

FIG. 14 illustrates a voltage threshold 532 at which an exemplary pain receptor (i.e. nerve) fires. As can be seen, threshold level 532 exceeds the reduced leading edge voltage 510 but is less than the plateau voltage 516. The shock voltage does not exceed threshold 532 until time 534. As such, the exemplary pain receptor does not fire until time 534. From that point until the end of the first phase 506 of the shock is only about 8 ms. Typically, pain receptors in the chest are not able to refire for at least 10 ms. That is, the pain receptors are usually refractory for at least 10 ms following excitation. Hence, a pain receptor that initially fires at time 534 is not likely able to refire until time 536. At that time, however, the voltage is far below the threshold and hence the pain receptor does not refire. Thus, even though the first phase of the shock is longer than the 10 ms refractory interval, pain receptors will fire, if at all, only once, thereby reducing perceived pain.

Note that voltage threshold 532 does not represent an average or mean triggering threshold for typical pain receptors. The peak voltage of the plateau-shaped shock is set well below the average triggering threshold for typical pain receptors, thus ensuring that most pain receptors do not fire at all and thereby achieving significant pain reduction. Threshold 532 instead represents the triggering threshold for one of the relatively few pain receptors that fires despite the relatively low voltage of the shock. As explained, the use of the reduced leading edge voltage helps ensure that the few pain receptors that fire despite the relatively low shock voltage will probably not fire a second time. Some pain receptors may have such low triggering thresholds that they fire immediately during the shock and hence are capable of firing again before the end of the first phase. Other pain receptors may have exceptionally short refractory periods. Thus, at least some pain receptors may fire twice despite the reduced leading edge voltage. Nevertheless, significant pain reduction can be achieved when using the reduced leading edge voltage as compared to the plateau-shaped shocks of FIGS. 6 and 7. This is in addition to the substantial pain reduction already achieved simply by using a relatively low voltage plateau-shaped shock. For shocks having a first phase with a duration less than 8 ms, the use of the reduced leading edge voltage is typically not warranted, since the entire first phase is less than the typical pain receptor refractory period and hence pain receptors are not likely to refire anyway.

Figure 15:
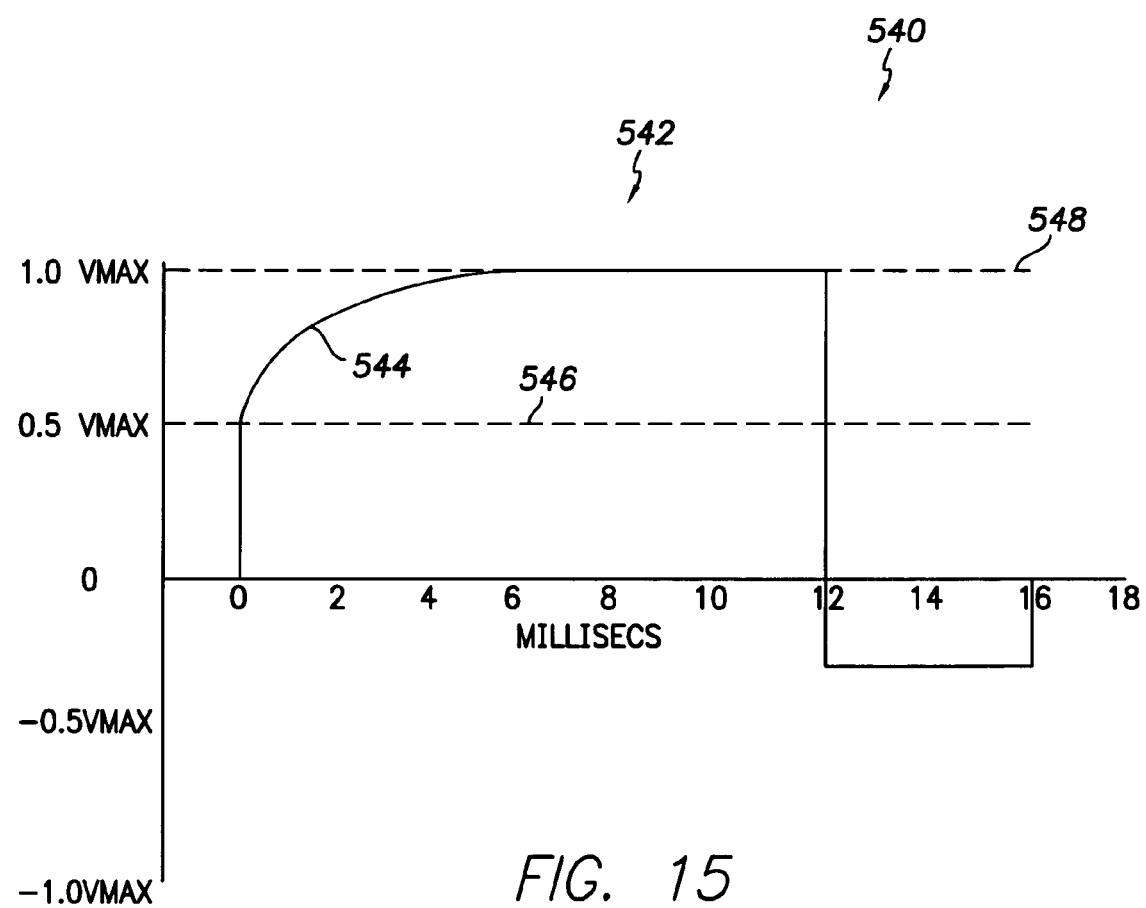
FIG. 15 is a graph illustrating a second exemplary plateau-shaped main cardioversion shock generated using the technique of FIGS. 12 and 13, wherein the shock voltage increases asymptotically from the leading edge voltage to the higher plateau voltage.
Figure 16:
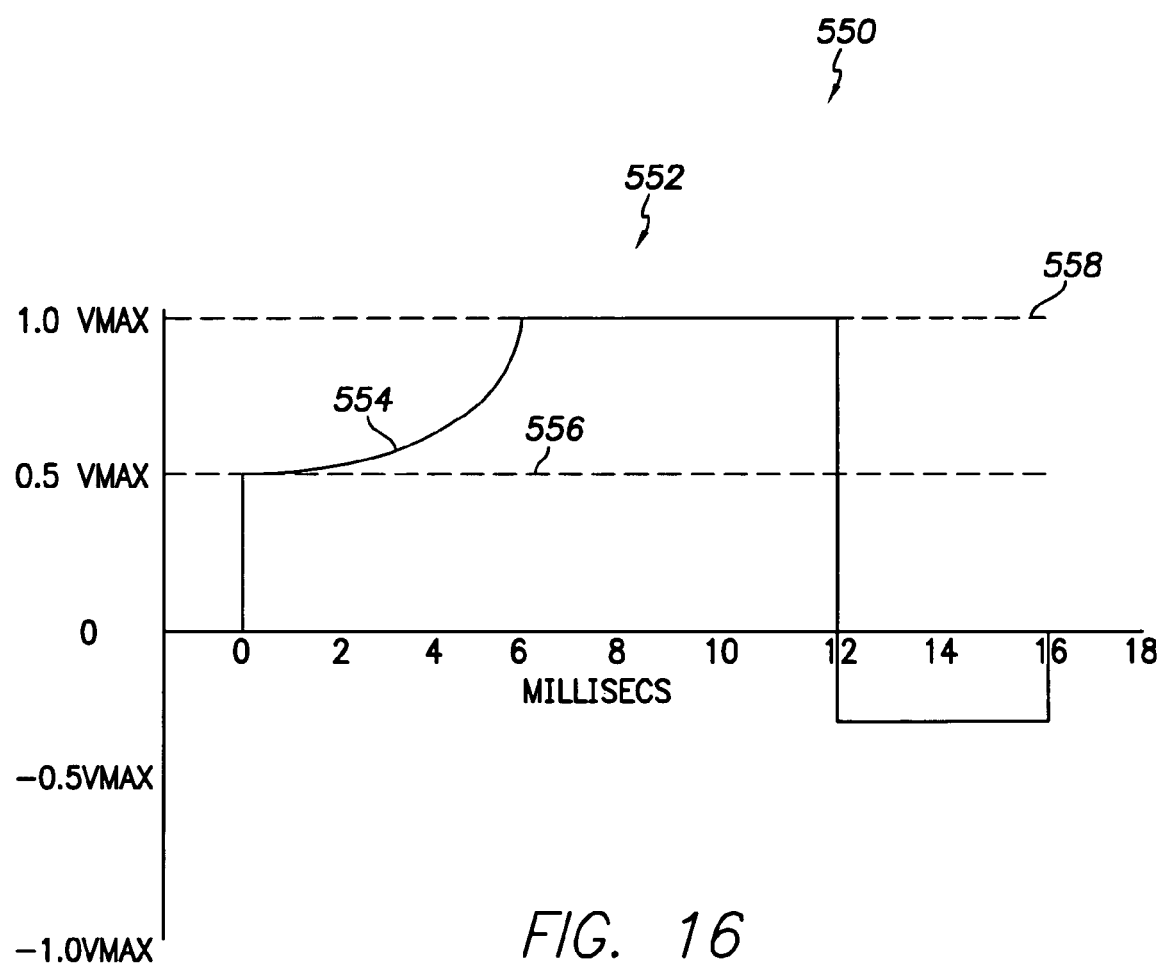
FIG. 16 is a graph illustrating a third exemplary plateau-shaped main cardioversion shock generated using the technique of FIGS. 12 and 13, wherein the shock voltage increases exponentially from the leading edge voltage to the higher plateau voltage.
Figure 17:
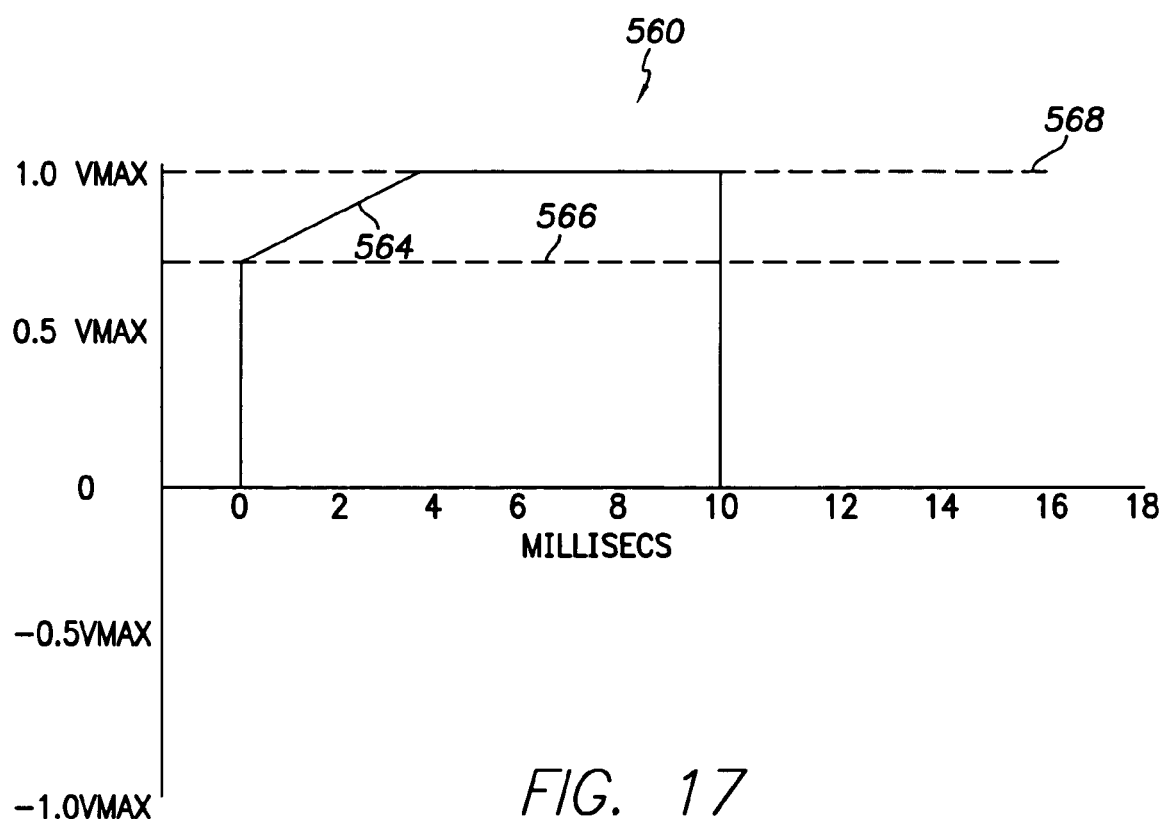
FIG. 17 is a graph illustrating a fourth exemplary plateau-shaped main cardioversion shock generated using the technique of FIGS. 12 and 13, which begins with a relatively high leading edge voltage and has a relatively long plateau portion.
Figure 18:
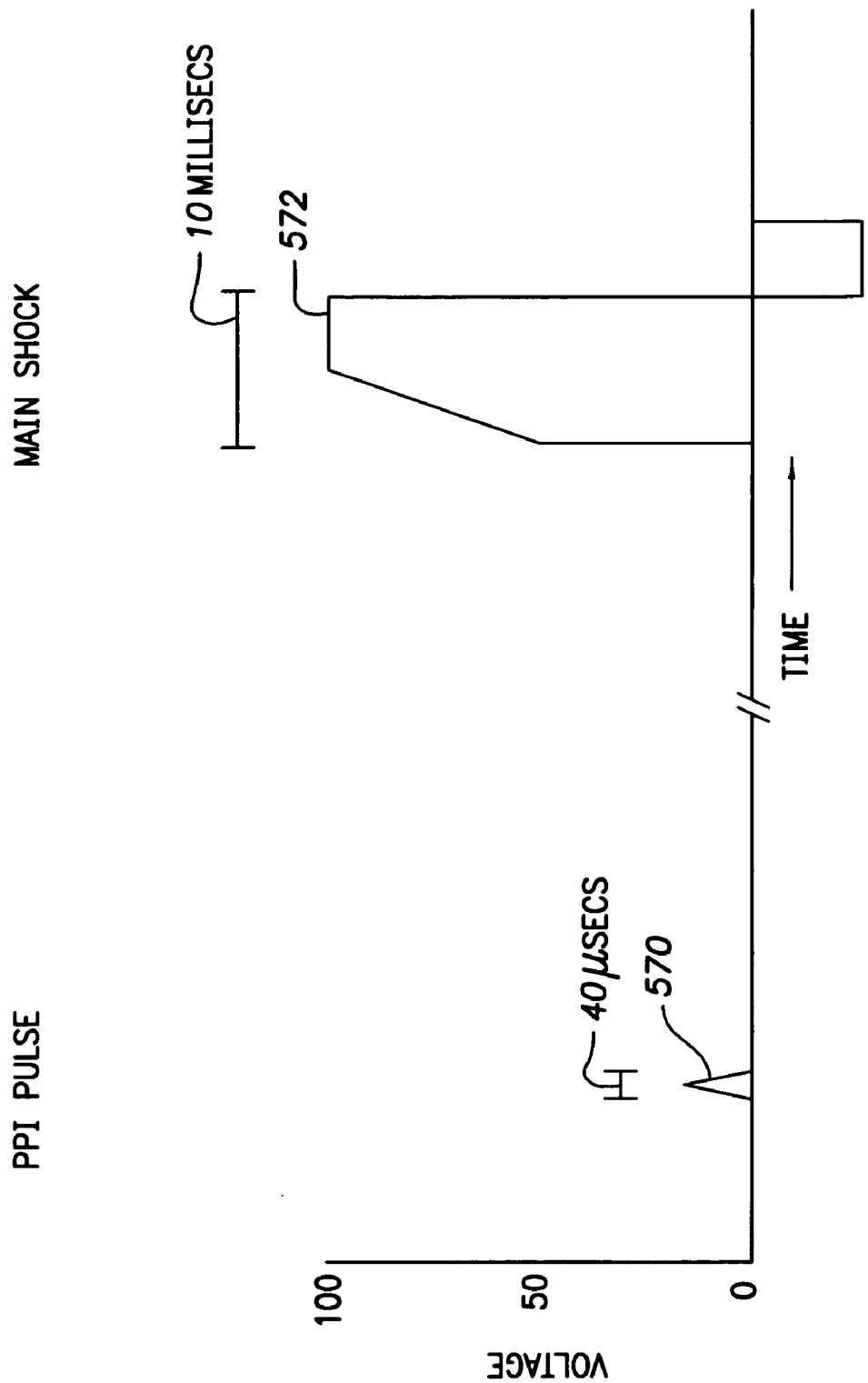
FIG. 18 is a graph illustrating an exemplary chevron-shaped PPI pulse generated using the technique of FIG. 6 followed by an exemplary plateau-shaped main cardioversion shock generated using the technique of FIGS. 12 and 13.

FIGS. 15-17 illustrate various shock waveforms with alternative shapes, each also having the reduced leading edge voltage. Briefly, FIG. 15 illustrates a waveform 540 having a first phase 542 wherein an initial gradually increasing portion 544 of the shock is curved (rather than linear as in FIG. 14.) More specifically, the gradual increase of the absolute magnitude of the shock voltage from the leading edge voltage 546 to the higher, plateau voltage 548 is asymptotic to the plateau voltage. That is, during interval 544, the shock voltage initially increases quickly from the reduced leading edge voltage 546. The rate of increase slows and gradually approaches the plateau voltage. FIG. 16 illustrates a waveform 550 having a first phase 552 wherein an initial portion 554 of the shock increases exponentially from the leading edge voltage 546 to the higher, plateau voltage 558. That is, during interval 554, the shock voltage initially increases slowly, then the rate of increase accelerates until reaching the plateau voltage 558, as shown. FIGS. 15-16 thus illustrate examples wherein, as with FIG. 15, the leading edge voltage is one half the plateau voltage and wherein the plateau portion begins midway through the first phase of the shock. FIG. 17 illustrates an alternative waveform wherein the leading edge voltage is higher and the plateau portion begins sooner. Also, the waveform of FIG. 17 is monophasic. More specifically, FIG. 17 illustrates a waveform 560 wherein the leading edge voltage 566 is about 70% of the plateau voltage 568 and wherein the interval 564 prior to the plateau comprises about 40% of the duration of the waveform, which is about 10 ms. Note that, in each of the examples shown, the voltage increases monotonically from the leading edge voltage up to the plateau voltage. This is not strictly necessary, as a monotonically increasing voltage is harder to generate using relatively simple shocking circuitry than a non-monotonically increasing voltage. In fact, the increasing section would be generated by chopping a higher voltage and varying the duty cycle of the chopping. This is then filtered but would still leave a ripple on the waveform.

The various parameters defining the shape, duration and magnitude of the shock waveform (including the plateau voltage and leading edge voltage levels) are preferably programmable or adjustable by the clinician. In one example, following device implant, the device is programmed to deliver shocks using default shock parameters, which the clinician can then optionally modify. Otherwise routine experimentation may be used to identify combinations of parameters that are particularly effective at reducing patient pain while still ensuring effective cardioversion. Preferably, the various parameters are set so as to minimize both delivered energy DFT and also voltage DFT, as discussed above in connection with FIGS. 4-11, while also reducing the number of pain receptors that fire twice during the shock, so as to achieve optimal pain reduction while still reliably defibrillating the atria or ventricles. Note also that the plateau-shaped main cardioversion waveforms of FIGS. 12-17 may be preceded by one or more PPI pulses to achieve still further pain reduction. This is illustrated by way of the example of FIG. 18. Briefly, FIG. 18 illustrates a chevron-shaped PPI pulse 570 preceding a plateau-shaped cardioversion shock 580 having a reduced leading edge voltage.

Insofar as circuitry for generating the plateau-shaped shock waveforms of FIGS. 12-18 is concerned, the general waveform shaping techniques set forth in U.S. patent application Ser. No. 10/687,386 of Moulder et al., cited above, may be exploited. Alternatively, the circuit described above in connection with FIG. 8 may be modified, if needed, to provide for generation of a plateau-shaped shock waveform with a reduced leading edge voltage. In this regard, the circuit can be modified to add another resistor after the capacitor but inside the electrode connections so as to provide for a starting voltage above zero.

Thus, what we have described are various techniques for pain reduction particularly for use in connection with the delivery of cardioversion shocks, including defibrillation shocks. As can be appreciated, a wide variety of techniques can be implemented consistent with the principles the invention and no attempt is made herein to describe all possible techniques. Moreover, although described primarily with reference to a combined pacer/defibrillator, the techniques of the invention may be exploited for use with non-pacing ICDs. Various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method for use with an implantable cardiac stimulation device for implant within a patient having a shocking circuit for generating therapeutic shocks for delivery to the patient, the method comprising:

generating an electrical therapeutic shock using the shocking circuit wherein the shock has a voltage waveform having a reduced leading edge voltage followed by a plateau voltage; and applying the shock to heart tissue of the patient wherein the step of generating the shock includes sharply increasing the absolute magnitude of the shock voltage from a baseline voltage to the leading edge voltage, wherein the increase is substantially instantaneous;

gradually increasing the absolute magnitude of the shock voltage from the leading edge voltage to a higher, plateau voltage, wherein the gradual increase occurs during a first extended interval of time;

maintaining the absolute magnitude of the shock voltage substantially at the plateau voltage for a second, extended interval of time; and dropping the absolute magnitude of the shock voltage back to the baseline voltage, wherein the drop is substantially instantaneous.

2. The method of claim 1 wherein the baseline voltage is zero.

3. The method of claim 1 wherein the polarity of the shock is positive such as that the plateau voltage is also positive.

4. The method of claim 1 wherein the polarity of the shock is negative such as that the plateau voltage is also negative.

5. The method of claim 1 wherein the gradual increase of the absolute magnitude of the shock voltage from the leading edge voltage to the higher, plateau voltage is monotonic.

6. The method of claim 5 wherein the gradual increase of the absolute magnitude of the shock voltage from the leading edge voltage to the higher, plateau voltage is asymptotic to the plateau voltage.

7. The method of claim 5 wherein the gradual increase of the absolute magnitude of the shock voltage from the leading edge voltage to the higher, plateau voltage is exponential from the leading voltage.

8. The method of claim 5 wherein the first and second intervals are substantially equal in duration.

9. The method of claim 1 wherein the first and second intervals have durations of the same order of magnitude.

10. The method of claim 1 wherein the leading edge voltage is in the range of 30% to 70% of the plateau voltage.

11. The method of claim 10 wherein the leading edge voltage is about 50% of the plateau voltage.

12. The method of claim 1 wherein the first interval comprises 20% to 80% of a total duration of a first phase of the shock comprising the first and second intervals.

13. The method of claim 12 wherein the first interval comprises about 50% of the total duration of the first phase of the shock.

14. The method of claim 1 wherein a first phase of the shock comprising the first and second intervals has a duration in the range of 8-15 milliseconds (ms).

15. The method of claim 1 wherein the step of generating the shock is performed to generate a monophasic waveform.

16. The method of claim 1 wherein the step of generating the shock is performed to generate a biphasic waveform and wherein a first phase of the biphasic waveform has the reduced leading edge voltage followed by the plateau voltage.

17. The method of claim 1 further including the initial step of generating and applying at least one pre-pulse pain inhibition (PPI) pulse prior to the step of generating the electrical therapeutic shock having the reduced leading edge voltage followed by the plateau voltage.

18. A system for use in an implantable cardiac stimulation device for implant within a patient, the system comprising:

means for detecting cardiac conditions indicating a need for a cardioversion shock;

means for generating an electrical therapeutic shock having a voltage waveform with a reduced leading edge voltage followed by a plateau voltage; and means for applying the shock to the heart tissue of the patient, wherein the means for generating an electrical therapeutic shock include means for sharply increasing the absolute magnitude of the shock voltage from a baseline voltage to the leading edge voltage, wherein the increase is substantially instantaneous;

means for gradually increasing the absolute magnitude of the shock voltage from the leading edge voltage to a higher, plateau voltage, wherein the gradual increase occurs during a first extended interval of time;

means for maintaining the absolute magnitude of the shock voltage substantially at the plateau voltage for a second, extended interval of time; and means for dropping the absolute magnitude of the shock voltage back to the baseline voltage, wherein the drop is substantially instantaneous.

\* \* \* \* \*